US 11,109,906 B2

(12) United States Patent
Vogt et al.

(10) Patent No.: US 11,109,906 B2
(45) Date of Patent: Sep. 7, 2021

(54) BONE CEMENT APPLICATOR WITH RETRACTABLE MIXING ROD AND METHOD FOR PRODUCTION OF A BONE CEMENT

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 196 days.

(21) Appl. No.: 16/443,307

(22) Filed: Jun. 17, 2019

(65) Prior Publication Data

US 2019/0380759 A1 Dec. 19, 2019

(30) Foreign Application Priority Data

Jun. 18, 2018 (DE) .................. 102018209784.4

(51) Int. Cl.
*A61B 17/88* (2006.01)
(52) U.S. Cl.
CPC .. *A61B 17/8822* (2013.01); *A61B 2017/8838* (2013.01)
(58) Field of Classification Search
CPC ............ A61B 17/8802; A61B 17/8811; A61B 17/8816; A61B 17/8822; A61B 17/8833; A61B 17/8838
See application file for complete search history.

(56) References Cited

U.S. PATENT DOCUMENTS

| 4,671,263 A | 6/1987 | Draenert |
| 4,758,096 A | 7/1988 | Gunnarsson |
| 4,973,168 A | 11/1990 | Chan |
| 5,100,241 A | 3/1992 | Chan |
| 5,344,232 A | 9/1994 | Nelson et al. |

(Continued)

FOREIGN PATENT DOCUMENTS

| DE | 3640279 | 6/1987 |
| DE | 102009031178 | 9/2010 |

(Continued)

OTHER PUBLICATIONS

Office Action dated Nov. 11, 2019 from corresponding European Patent Application No. 19176769.8.

(Continued)

*Primary Examiner* — Matthew J Lawson
(74) *Attorney, Agent, or Firm* — Stradley Ronon Stevens and Young, LLP

(57) ABSTRACT

A bone cement applicator comprising a cartridge with an internal space. The cartridge has a head with a dispensing opening for expulsion of bone cement, a dispensing plunger, a receptacle mobile in the cartridge, and a mixing rod with a mixer fastened to it and arranged in the internal space of the cartridge. The mixing rod is detachably connected, on a side opposite from the mixer, to a front side of the receptacle that faces the cartridge head. When the mixing rod is detached from the receptacle and the receptacle is propelled in the direction of the cartridge head the mixing rod can be pushed into the receptacle. A method is also disclosed for production of a bone cement using the bone cement applicator.

20 Claims, 12 Drawing Sheets

(56) References Cited

U.S. PATENT DOCUMENTS

| | | | |
|---|---|---|---|
| 5,551,778 | A | 9/1996 | Hauke et al. |
| 5,586,821 | A | 12/1996 | Bonitati et al. |
| 5,588,745 | A | 12/1996 | Tanaka et al. |
| 5,624,184 | A | 4/1997 | Chan |
| 5,997,544 | A | 12/1999 | Nies et al. |
| 6,033,105 | A | 3/2000 | Barker et al. |
| 6,709,149 | B1 | 3/2004 | Tepic |
| 8,757,866 | B2 | 6/2014 | Vogt et al. |
| 2003/0021180 | A1 | 1/2003 | Wahlig et al. |
| 2007/0041267 | A1* | 2/2007 | Coffeen ............... B01F 13/002 366/189 |
| 2008/0312588 | A1* | 12/2008 | Faccioli ............ B01F 15/0205 604/87 |
| 2012/0155214 | A1* | 6/2012 | Faccioli ............ A61B 17/8825 366/130 |
| 2016/0278836 | A1* | 9/2016 | Foster ............... A61B 17/8819 |
| 2018/0132919 | A1 | 5/2018 | Vogt et al. |
| 2019/0038331 | A1* | 2/2019 | Purdy ...................... B01F 5/00 |
| 2019/0183552 | A1* | 6/2019 | Kluge ................ B01F 15/0237 |
| 2019/0380758 | A1* | 12/2019 | Vogt ................... B01F 11/0082 |
| 2020/0179024 | A1* | 6/2020 | Vogt ................... A61B 17/8833 |
| 2021/0022785 | A1* | 1/2021 | Hsueh ............... A61B 17/8825 |

FOREIGN PATENT DOCUMENTS

| | | |
|---|---|---|
| DE | 102016121607 | 5/2018 |
| EP | 0692229 | 1/1996 |
| EP | 0796653 | 9/1997 |
| EP | 1005901 | 6/2000 |
| EP | 1016452 | 7/2000 |
| EP | 1020167 | 7/2000 |
| EP | 1886647 | 2/2008 |
| WO | 9426403 | 11/1994 |
| WO | 9718031 | 5/1997 |
| WO | 9922854 | 5/1999 |
| WO | 9967015 | 12/1999 |
| WO | 0035506 | 6/2000 |
| WO | 2011089480 | 7/2011 |

OTHER PUBLICATIONS

Charnley, "Anchorage of the femoral head prosthesis of the shaft of the femur", The Journal of Bone and Joint Surgery, 1960, 42, pp. 28-30.

Office Action (and English translation) dated Jan. 18, 2019 from counterpart German Patent Application No. 102018209784.4.

* cited by examiner

BONE CEMENT APPLICATOR WITH RETRACTABLE MIXING ROD AND METHOD FOR PRODUCTION OF A BONE CEMENT

RELATED APPLICATION

This application claims the benefit of priority to German Patent Application Number DE 102018 209784.4, filed on Jun. 18, 2018, the contents of which are incorporated in this application by reference.

TECHNICAL FIELD

The invention relates to a bone cement applicator for storage and mixing of a bone cement powder and a monomer liquid as well as for applying a pasty bone cement mixed together from the bone cement powder and the monomer liquid. The invention also relates to a method for production of a bone cement using the bone cement applicator.

BACKGROUND OF THE DISCLOSURE

Polymethylmethacrylate (PMMA) bone cements are based on the pioneering work of Sir Charnley. Charnley, J., "Anchorage of the femoral head prosthesis of the shaft of the femur," J. Bone Joint Surg. 42, 28-30 (1960). Conventional PMMA bone cements consist of a liquid monomer component and a powder component. The monomer component generally contains the monomer, methylmethacrylate, and an activator (N,N-dimethyl-p-toluidine) dissolved in the monomer. The powder component, also called bone cement powder, comprises one or more polymers that are produced through polymerization, preferably suspension polymerization, based on methylmethacrylate and co-monomers, such as styrene, methylacrylate, or similar monomers, a radiopaquer, and the initiator, dibenzoylperoxide. Mixing the powder component and the monomer component and swelling of the polymers of the powder component in the methylmethacrylate generates dough that can be shaped plastically and is the actual bone cement or bone cement dough. During the mixing of the powder component and the monomer component, the activator, N,N-dimethyl-p-toluidine, reacts with dibenzoylperoxide while forming radicals. The radicals thus formed trigger the radical polymerization of the methylmethacrylate. Upon advancing polymerization of the methylmethacrylate, the viscosity of the bone cement dough increases until the bone cement dough solidifies.

PMMA bone cements can be mixed by mixing the bone cement powder and the monomer liquid in suitable mixing beakers with the aid of spatulas. This can lead to air bubbles being enclosed in the bone cement dough, which can have a negative effect on the mechanical properties of the cured bone cement.

A large number of vacuum cementing systems have been described for preventing air inclusions in bone cement dough of which the following are identified for exemplary purposes: U.S. Pat. Nos. 6,033,105 A, 5,624,184 A, 4,671, 263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, EP 1 886 647 A1, and U.S. Pat. No. 5,344,232 A. These mixing systems contain, for mixing of the cement components, a mixing rod that can be operated manually from outside and has mixing vanes as mixers attached to it. External vacuum pumps are required for generation of the vacuum. These vacuum pumps are generally driven by compressed air and generate a vacuum according to the Venturi principle. Manually driven extrusion devices are used for extrusion of the mixed bone cement from the cartridges. These extrusion devices can be connected reversibly to the cartridges for extrusion of the cement dough. Following the extrusion process, the extrusion devices are separated from the cartridges, cleaned, and re-sterilized. The spent cartridges are discarded.

Cementing systems in which both the bone cement powder and the monomer liquid are already packed in separate compartments of the mixing devices and are mixed with each other in the cementing system only right before application of the cement are a development of cementing technology. Such closed full-prepacked mixing devices have been proposed in EP 0 692 229 A1, DE 10 2009 031 178 B3, U.S. Pat. Nos. 5,997,544 A, 6,709,149 B1, WO 00/35506 A1, EP 0 796 653 A2, and U.S. Pat. No. 5,588,745 A.

Patent DE 10 2009 031 178 B3 discloses a storage and mixing device as a full-prepacked mixing device, in which the starting components required for the production of the bone cement are already stored in the storage and mixing device and can be combined and mixed in the storage and mixing device. The storage and mixing device comprises a two-part dispensing plunger for closing a cement cartridge. A combination of a gas-permeable sterilization plunger and a gas-impermeable sealing plunger is used in this context. This principle of a closed vacuum mixing system is implemented in the closed cementing system made and distributed under the brand name PALACOS® PRO by Heraeus Medical GmbH. For the monomer transfer and the mixing in a vacuum, an external vacuum pump is required that is usually driven by compressed air. Likewise, a separate manually operable extrusion device is used for extruding the mixed cement dough.

DE 10 2016 121 607 A1 proposes a full-prepacked mixing system with a cartridge containing a bone cement powder for production of a bone cement. A dispensing plunger is provided in the cartridge and a receptacle containing a monomer liquid container is arranged downstream from the cartridge. A dispensing plunger is situated on the rear side of the receptacle and can be used to crush the monomer liquid container and to extrude the monomer liquid from the receptacle into the cartridge. This system involves no manual mixing of the starting components by a mixer.

In the vacuum mixing systems with mixers referred to thus far, the mixing of the cement components must be followed by the mixing rod having to be broken off or pulled out of the mixing system before application of the bone cement. Accordingly, the known methods and devices are disadvantageous in that the process of breaking off the mixing rod may be associated with leakage of the bone cement applicator and in that the processes of breaking off and pulling out the mixing rod are always required as additional working steps. Moreover, the broken off mixing rod litters the operating room or "OR" theater as another separate part that needs to be discarded. Bone cement applicators without a mixer require much effort for the bone cement to be mixed sufficiently. Moreover, it is also possible that parts of the bone cement are not mixed sufficiently. These parts need to be removed or there may be an adverse effect on the quality of the bone cement.

SUMMARY OF THE INVENTION

The subject matter of the invention is a bone cement applicator for storage, mixing, and application of bone cement. The bone cement applicator is preferably implemented in the form of a closed prepack mixing system with an integrated extrusion device. The bone cement applicator is preferably well-suited and/or intended for arthroplasty, vertebroplasty, and kyphoplasty. Methods for the mixing and application of polymethylmethacrylate bone cement are proposed for this purpose as well.

It is an object of the invention to develop a bone cement applicator for storage, mixing, and application of polymethylmethacrylate bone cement by which the disadvantages of the prior art can be overcome. The bone cement powder and the monomer liquid are to be stored in separate compartments in the bone cement applicator before being mixed. The monomer transfer from the monomer liquid container into the bone cement powder takes place without the application of an externally provided vacuum. The mixing takes place appropriately in the closed device using a mixing rod with a mixer such that the medical user is not exposed directly to the bone cement powder or the monomer liquid. After the cement components are mixed, the step of removing the mixing rod from the mixing system by pulling out and/or breaking off the mixing rod is omitted. The bone cement thus produced can be manually extruded from the bone cement applicator without an external extrusion device having to be connected to the device.

It is therefore an object of the invention to develop a completely autonomous prepack mixing system that permits the cement components to be mixed and the mixed bone cement to be extruded without additional devices, such as external vacuum pumps and extrusion devices, being required.

The objects of the invention are met by a bone cement applicator for storage and mixing of a bone cement powder and a monomer liquid as well as for applying a pasty bone cement mixed together from the bone cement powder and the monomer liquid, the bone cement applicator comprising:

(A) a cartridge with a cylindrical internal space for mixing of the bone cement, whereby the cartridge comprises, on a front side, a cartridge head with a dispensing opening for expelling the bone cement from the internal space;

(B) a dispensing plunger for expelling the mixed bone cement from the internal space through the dispensing opening, whereby the dispensing plunger is arranged in the internal space of the cartridge such as to be mobile along the cylinder axis of the internal space in the direction of the cartridge head, whereby the bone cement powder is contained between the dispensing plunger and the cartridge head in the internal space of the cartridge;

(C) a receptacle, whereby a monomer liquid container is arranged on the inside of the receptacle, whereby the monomer liquid container contains the monomer liquid and can be opened on the inside of the receptacle, whereby the receptacle is inserted into the cartridge on a rear side of the cartridge that is opposite from the front side of the cartridge, and is mobile in the cartridge; and (D) a mixing rod, whereby the mixing rod with a mixer fastened to it is arranged in the internal space of the cartridge, whereby the mixer is fastened to a front side of the mixing rod that faces the cartridge head, whereby the mixing rod is connected, on a side opposite from the mixer, to a front side of the receptacle that faces the cartridge head, such that the mixing rod with the mixer can be moved in the internal space for mixing of the bone cement powder with the monomer liquid through a motion of the receptacle against the cartridge, and whereby the mixing rod is connected to the receptacle so as to be detachable, and the mixing rod detached from the receptacle can be pushed into the receptacle when the receptacle is propelled in the direction of the cartridge head.

Preferably, the receptacle is at least axially mobile in the cartridge in the direction of the cylinder axis of the internal space. In this context, it is particularly preferable that at least regions of the receptacle can be inserted or screwed into the internal space of the cartridge.

The receptacle is preferred to be an ampoule holder.

The invention can provide a part of the receptacle with the mixing rod, in particular a closure of the receptacle that faces the cartridge head, to detach from the remaining receptacle.

Preferably, the monomer liquid container is an ampoule made of glass or a plastic material. Ampoules made of glass or plastic can be opened particularly reliably. Moreover, the monomer liquid can be stored in the ampoule as a monomer liquid container for particularly long periods of time. Alternative monomer liquid containers can be, for example, coated film bags.

The receptacle is preferably designed as an ampoule holder. It is particularly preferred in this context for the ampoule holder to be suitable and provided for holding an ampoule made of glass or plastic.

The internal space of the cartridge has a cylindrical geometry with a circular footprint. The cylindrical shape is the simplest shape by means of which the internal space of the cartridge can be implemented. A cylindrical shape shall be understood geometrically to mean the shape of a general cylinder of any footprint, i.e. not just a cylinder having a circular footprint. But the internal space of the cartridge needs to have a rotationally symmetrical symmetry, meaning a cylindrical shape with a circular footprint, since it would otherwise not be possible to screw the receptacle in or to adequately seal the receptacle on its front side with respect to the internal wall of the internal space.

The invention can preferably provide the dispensing opening for storage and mixing to be closed by a closure that can be opened. This configuration provides a closed prepack mixing system.

In this context, the invention can provide the closure to be connected to the cartridge head in a detachable manner by a thread or a bayonet closure.

The invention can provide the closure to close the dispensing opening in a liquid-tight manner or in a gas-tight and liquid-tight manner.

This configuration ensures that no bone cement powder, no monomer liquid, and no bone cement can leak from the internal space of the cartridge while the bone cement is being mixed.

With the exception of the starting components, the monomer liquid container, and any seals that may be present, all parts of the bone cement applicator preferably consist of plastic, in particular a thermoplastic material. If the monomer liquid container consists of a plastic material, it needs to consist of a brittle breakable plastic material. The seals preferably consist of silicon or rubber.

The invention can provide the mixing rod to be detachable from the receptacle by pressing onto the mixer touching against the cartridge head, and/or by rotating or screwing the receptacle against the mixer, which is secured against a rotation in the internal space.

By this design, the mixing rod can be detached from the receptacle by moving the receptacle against the mixer, which is affixed in the area of the cartridge head. There is then no need to have a separate device for detachment of the mixing rod from the dispensing plunger. This simplifies the design of the bone cement applicator.

Moreover, the front side of the receptacle can form the dispensing plunger for expelling the bone cement out of the internal space, whereby the dispensing plunger is preferred to be cylindrical.

As a result, the mixing rod does not need to be guided through a separate dispensing plunger so as to be mobile in the direction of the cylinder axis of the internal space. This is disadvantageous, though, in that the area of the internal space bordering the front side of the dispensing plunger cannot be reached by the mixer and there consequently no mixing takes place in this area. However, if the bone cement applicator is held with the cartridge head downwards, the bone cement powder and the leaking monomer liquid collect in the front area of the internal space bordering on the cartridge head due to the effect of gravity and can therefore be reached and mixed by the mixer. Moreover, the part of the bone cement that is mixed most poorly can be retained in the bone cement applicator, for example in a dead volume of the cartridge.

As an alternative, the invention can provide the internal space with the dispensing plunger to be separated into a front part and a rear part, whereby the front part of the internal space is bordered by the cartridge head and the dispensing plunger and the rear part of the internal space is bordered by the dispensing plunger and the receptacle, whereby the mixing rod is guided through a feedthrough in the dispensing plunger and is supported so as to be axially mobile in the feedthrough, whereby the mixer and the bone cement powder are arranged in the front part of the internal space, and whereby the dispensing plunger can be pushed in the direction of the cartridge head by the receptacle.

By this design, it can be ensured that the entire front part of the internal space, in which the bone cement is mixed, can be reached by the mixer and can thus be mixed. For this purpose, the mixer can preferably be pulled up to the dispensing plunger. As a result, all areas of the front part of the internal space can be reached by the mixer and a well-mixed bone cement can be produced with the bone cement applicator.

Preferably, the dispensing plunger comprises a channel that is covered by a pore disk or has a pore disk arranged in it, or the dispensing plunger comprises multiple channels that are covered by a pore disk or have a pore disk each arranged in them. The channel or channels then connects or connect the front part of the internal space to the rear part of the internal space, whereby the connection is permeable to the monomer liquid and gases, but is impermeable to the bone cement powder due to the pore filter or other measures.

If the dispensing plunger is provided as a separate part in the internal space of the cartridge, the dispensing plunger can be affixed to the cartridge in a press-fit in the internal space, whereby the dispensing plunger preferably comprises a cylindrical or circular external circumference that matches the internal space.

This design allows, on the one hand, the mixing rod to glide through the dispensing plunger without the dispensing plunger being moved against the cartridge, but, on the other hand, the dispensing plunger can be pushed in the direction of the cartridge head by the receptacle without too much resistance in order to extrude the bone cement out of the cartridge and to degas the bone cement through the dispensing plunger.

Moreover, the invention can prevent movement of the dispensing plunger within the internal space through a motion of the mixing rod in the feedthrough in the dispensing plunger.

This configuration ensures that the mixer can reach all areas of the front part of the internal space of the cartridge and that, thus, good mixing of the bone cement can be attained.

According to a preferred embodiment, the dispensing plunger comprises at least one channel that is impermeable to the bone cement powder and is permeable to the monomer liquid and gases.

By this design, the monomer liquid can flow through the dispensing plunger to the bone cement powder without the bone cement powder having to move in the direction of the monomer liquid container. This configuration ensures that the bone cement is produced only in the part of the internal space between the dispensing plunger and the cartridge head.

Moreover, according to the invention, the receptacle can be inserted into the internal space up to a first limit stop that is formed by an external thread on the receptacle and can be screwed, up to a second limit stop, by the external thread into an internal thread in the cartridge on the rear side thereof or into an internal thread in a ring on the rear side of the cartridge, whereby the mixing rod cannot be detached from the receptacle during a motion of the receptacle up to the first limit stop and the mixing rod can be detached from the receptacle by screwing the receptacle into the cartridge.

By this design, the bone cement applicator can be operated easily. What this also attains is that the mixing rod is not already detached from the receptacle while the bone cement is being mixed, but only during the extrusion of the mixed bone cement, which takes place by screwing the receptacle into the cartridge, i.e., into the internal thread on the rear side of the cartridge or into the internal thread on the ring.

The invention can just as well provide an opening facility, which can be operated from outside and can be used to open the monomer liquid container on the inside of the receptacle, to be arranged on the receptacle.

By this design, the monomer liquid container can be opened from outside, but simultaneously inside the receptacle. This prevents the user from being exposed to the monomer liquid and prevents the monomer liquid that is intended and needed for the production of a bone cement from getting lost.

In this context, the monomer liquid container can be opened by inserting or screwing the opening facility into the receptacle, whereby the monomer liquid container is situated on the inside of the receptacle.

By this design, the entire bone cement applicator can be operated by pushing and/or screwing-in its parts (the opening facility into the receptacle and the receptacle into the cartridge). By this design, the bone cement applicator is particularly easy to use.

In this context, the monomer liquid container can be an ampoule made of glass or a plastic material, whereby the ampoule comprises an ampoule head, a cylindrical ampoule body, and an ampoule base situated opposite from the ampoule head, whereby the ampoule head has a smaller diameter than the ampoule body and is connected to the ampoule body by shoulders, whereby the opening facility comprises a sleeve that pushes onto the shoulders of the ampoule during the insertion or screwing-in.

The sleeve is preferably implemented in the form of a hollow cylinder, whereby an opening for gas exchange can be provided in order to prevent any overpressure in the bone cement applicator.

A uniform pressure can be exerted onto the ampoule by the sleeve and a reproducible opening of the ampoule can thus be attained.

Because the opening facility comprises a sleeve that pushes onto the shoulders of the ampoule during the insertion and/or screwing-in, the ampoule base is pushed onto a projection on the inside of the receptacle and the ampoule is thus opened at the ampoule base allowing the monomer liquid to flow out.

In this context, the sleeve of the opening facility can project out of the receptacle on the side opposite from the cartridge head, whereby the sleeve preferably projects sufficiently far out of the receptacle such that fully inserting or screwing the sleeve into the receptacle is assured to fracture the ampoule.

By this design, the sleeve can be pushed particularly easily into the receptacle and the ampoule can thus be opened.

Moreover, the invention can provide the opening facility to comprise a closure cap that can be screwed onto the rear side of the receptacle in the direction of the cartridge head, whereby the closure cap, being screwed in the direction of the cartridge head, pushes the sleeve into the receptacle and thus opens the ampoule on the inside of the receptacle.

The closure cap getting screwed on allows the sleeve to be pushed into the receptacle with great force and thus allows even a stable ampoule made of glass to be opened.

Moreover, the invention can provide the closure cap to comprise an internal thread and the receptacle to comprise a matching rear-side external thread, and the inside of the closure cap to form a limit stop for the receptacle.

The distance between the limit stop and the end of the internal thread of the closure cap that faces the cartridge head corresponds to the full and/or maximal pitch of the internal thread of the closure cap.

This design allows a particularly compact bone cement applicator to be provided that can be operated easily and reliably.

Moreover, at least one gas supply opening is provided in the wall of the receptacle that connects the inside of the receptacle to the surroundings of the bone cement applicator, whereby the at least one gas supply opening can be closed by inserting or screwing the opening facility in, in particular can be closed by inserting or screwing the sleeve in.

Via the gas supply openings, the inside of the receptacle and, through a connection, the internal space of the cartridge of the bone cement applicator as well can be sterilized with a sterilizing gas, such as ethylene oxide. Concurrently, the gas supply opening is closed by the sleeve before the monomer liquid container is opened such that no monomer liquid can leak towards outside through the gas supply openings.

The inside of the receptacle can be connected in a liquid-permeable manner to the internal space of the cartridge, whereby, preferably, the front side of the receptacle facing the cartridge head comprises at least one liquid-permeable passage, and the dispensing plunger comprises at least one liquid-permeable channel for this purpose.

Upon appropriate positioning of the bone cement applicator (with the cartridge head facing downward), this orientation ensures that the monomer liquid can readily flow out of the receptacle into the internal space of the cartridge between the dispensing plunger and the cartridge head.

Preferably, the inside of the receptacle is connected to the internal space of the cartridge in a liquid-permeable manner, but impermeable to the bone cement powder, whereby the dispensing plunger particularly preferably comprises at least one liquid-permeable and bone cement powder-impermeable channel. For this purpose, it is particularly preferred to have a pore disk arranged on or in the dispensing plunger.

For easier assembly of the bone cement applicator, the cartridge head can be a cartridge lid that can be screwed onto the cartridge, whereby the cartridge lid seals the internal space of the cartridge at the front side thereof in a gas-tight and liquid-tight manner, and whereby the dispensing opening is arranged in the cartridge lid.

This design allows the bone cement applicator to be assembled particularly easily and inexpensively. Accordingly, other parts of the bone cement applicator can be inserted easily into the otherwise cylindrical cartridge before the cartridge head closes off the cartridge.

Moreover, the invention can provide the cartridge to comprise, on its rear side, an internal thread and/or a ring with an internal thread that allows the receptacle to be screwed in, whereby an external thread matching the internal thread of the cartridge or the internal thread of the ring is provided on the receptacle.

By this design, the receptacle can be forcefully propelled in the internal space of the cartridge such that the mixing rod can be conveniently detached from the receptacle.

Moreover, the invention can provide a mandrel for opening of the monomer liquid container to be arranged on the side of the receptacle that points into the inside of the receptacle.

By this design, the monomer liquid container can be opened at a defined place inside the receptacle.

In this context, the mixing rod can extend all the way into the mandrel and the mixing rod can push through the mandrel, when the mixing rod detaches from the receptacle, or the mandrel can be an extension of the mixing rod and the mandrel can separate from the receptacle as well when the mixing rod detaches from the receptacle.

These two measures allow the mixing rod to be pushed reliably into the receptacle while the bone cement is being dispensed from the internal space of the cartridge, without the mixing rod becoming lodged in the receptacle while this is ongoing, such as, for example, on fragments of the opened monomer liquid container.

Accordingly, the invention can provide the mixing rod in the receptacle to be appropriately arranged within a mandrel that points into the inside of the receptacle such that the mixing rod can be pushed through the mandrel into the inside of the receptacle.

By this design, the mixing rod is pushed in targeted manner through the opening in the monomer liquid container produced by the mandrel and into the monomer liquid container. For this purpose, the mixing rod is preferably manufactured from a harder material than the mandrel and the receptacle. For example, the mixing rod can consist of metal and the mandrel with the receptacle can consist of a plastic material.

The mixing rod can comprise, in its connection to the receptacle, a circular disk with an external thread, whereby the circular disk is screwed into a matching internal thread on the front side of the receptacle that faces the cartridge head, whereby the external thread of the circular disk and the internal thread on the front side of the receptacle are preferred to be left-hand threads.

By this design, the mixing rod with the circular disk can be separated from the front side of the receptacle through a left-hand turn, and the mixing rod with the circular disk can be pushed into the inside of the receptacle, when the receptacle is being pushed or screwed into the internal space of the cartridge.

The invention can provide the dispensing plunger to be sealed with respect to the lateral internal walls of the internal space such that the dispensing plunger is mobile in a gas-tight manner within the internal space.

By this design, the bone cement cannot be squeezed out of the bone cement applicator between the dispensing plunger and the internal wall of the cartridge. Moreover, a negative pressure can be generated in the internal space of the cartridge through a motion of the dispensing plunger.

Preferably, the invention can just as well provide the receptacle to have a larger diameter on its rear side opposite from the cartridge head than the internal space of the cartridge.

This configuration implements a limit stop up to which the receptacle can be moved into the internal space of the cartridge. By this design, the receptacle can be prevented from being pushed against the cartridge head with great force and from thus deforming the cartridge head via the mixer and, in the process, from inadvertently fracturing the bone cement applicator at these places.

According to a particularly preferred embodiment, the present invention can provide a ring with a thread, preferably with an internal thread, to be arranged on the rear side of the cartridge, whereby the receptacle comprises a counter thread that matches the thread of the ring, in particular a matching external thread, and whereby the ring is connected to the cartridge so as to be mobile by shifting or screwing it against the cartridge in the axial direction with respect to the cylinder axis of the cylindrical internal space of the cartridge.

By this design, the receptacle can be screwed into the thread of the ring and can thus be pushed into the internal space of the cartridge, even when the mixer of the mixing rod touches against the cartridge head in the internal space, and the counter thread of the receptacle forms a limit stop for the receptacle by pulling or screwing the ring away from the cartridge head such that the counter thread of the receptacle engages the thread of the ring and can thus be screwed into the cartridge.

Accordingly, the purpose of the ring that can be shifted or screwed is to allow the receptacle to be inserted into the internal space so deeply during the mixing process that the internal wall of the cartridge head is scraped by the mixer. The external thread of the receptacle must not yet engage the thread on the rear side of the cartridge and/or of the ring while the mixing is ongoing, because manual mixing would otherwise not be possible. However, after the mixing process, the counter thread of the receptacle must be made to engage the thread of the ring on the cartridge or of a device fastened to it. There seems to be a conflict between this requirement and the free axial mobility of the receptacle for the mixing of the content of the internal space of the cartridge. Moreover, a relatively strong force is required for pushing the mixing rod through the hollow mandrel. This means that either the user first needs to move the receptacle against the cartridge head with brute force in order to puncture the mixing rod through the mandrel and make the receptacle engage the thread on the rear side of the cartridge or there must be a device present that establishes a connection between the cartridge and the receptacle after the mixing process is completed such that the receptacle is made to engage the thread on the rear side of the cartridge. For a "force-free" connection without hitting with a hammer, the ring possessing the thread is arranged such that it can be shifted or screwed onto the cartridge in the longitudinal direction.

The ring can be provided as a sliding ring or a threaded ring.

Referring to bone cement applicators with a ring, the invention can provide a limit stop for the ring on the rear side of the cartridge beyond which the ring cannot be moved in the direction away from the cartridge head such that the ring can be shifted or screwed axially in the direction away from the cartridge head only for a limited distance.

By this design, the ring cannot be detached from the cartridge and the receptacle can be screwed into the cartridge via the ring as a connector.

The ring is preferably secured against torsion by fins, if it is fastened to the cartridge so as to be shiftable, i.e., if it is provided as a sliding ring. During application, the user pushes the receptacle as far as possible against the cartridge head after the mixing takes place. Then the user shifts the shiftable sliding ring or screws the screw-type threaded ring in the direction of the receptacle. Then, the user screws the receptacle into the thread of the ring and screws the receptacle in the direction of the cartridge head. First, the mixing rod is pushed through the hollow mandrel and/or is separated from the receptacle. Then, if applicable, the receptacle pushes onto the separate dispensing plunger and, after opening the cartridge head, extrudes the cement dough out of the dispensing opening in the cartridge head that has been opened for this purpose. During the forward motion of the receptacle in the direction of the cartridge head, the mixing rod dips into the receptacle and/or into the emptied monomer liquid container. Finally, the sliding ring shifts in the direction of the cartridge head until the dispensing plunger hits against the rear side of the mixer.

The second variant with a threaded ring (threaded sleeve) works in the same way. The difference is that the threaded ring is rotated, rather than pushed, on the external thread of the cartridge in the direction of the ampoule holder after the mixing process takes place. Finally, the threaded ring rotates along in the direction of the cartridge head until the plunger with the pore disk hits against the rear side of the mixer.

The objects underlying the present invention are also met by a method for the production of a bone cement using a bone cement applicator according to the invention, comprising the following steps of:

(A) opening the monomer liquid container on the inside of the receptacle, and the monomer liquid flowing out of the monomer liquid container, whereby the monomer liquid flows out of the receptacle into the bone cement powder in the internal space of the cartridge;

(B) alternating pulling and pushing the receptacle out of and into the internal space of the cartridge, whereby that motion moves the mixer in the internal space of the cartridge and thus the bone cement powder and the monomer liquid are mixed together to form the bone cement;

(C) detaching the mixing rod from the receptacle by a screw motion or rotational motion of the receptacle against the cartridge and/or by pressing the receptacle into the internal space of the cartridge;

(D) opening the dispensing opening; and (E) extruding the bone cement out of the internal space of the cartridge through the opened dispensing opening, whereby the bone cement is extruded out of the internal space of the cartridge by the dispensing plunger and the dispensing plunger is driven by pushing or screwing the receptacle into the internal space of the cartridge, and whereby the mixing rod is pushed into the receptacle.

Referring to bone cements with a lower viscosity, the receptacle can first be pulled out of the internal space of the cartridge and, therefore, the mixer can initially be pulled away from the cartridge head in the direction of the rear side of the internal space of the cartridge. Referring to bone cements with a higher viscosity, the receptacle needs to be pushed into the internal space of the cartridge initially and, in the process, the mixer needs to be pushed initially from the rear side in the direction of the cartridge head. This prevents a stable gel layer from being generated at the junction as a reaction product of the bone cement powder and the monomer liquid, when the monomer liquid is supplied, which can no longer be penetrated by the supply of more monomer liquid.

The invention can provide the dispensing plunger to be arranged as a separate part in the internal space of the cartridge and the dispensing plunger to comprise at least one channel that is impermeable to the bone cement powder and is permeable to the monomer liquid and gases, whereby the monomer liquid, in step (A), flows through the dispensing plunger into the front part of the internal space of the cartridge that is bordered by the dispensing plunger and the cartridge head, the mixing rod, in step (B), moves through a feedthrough in the dispensing plunger, and the dispensing plunger, in step (E), is pushed in the direction of the cartridge head by the receptacle.

This ensures that the bone cement powder can be completely mixed with the monomer liquid.

In this context, the a gas contained in the bone cement in step (E) can be extruded from the bone cement through the at least one channel in the dispensing plunger, when the receptacle is pushed into or screwed into the internal space of the cartridge.

By this design, the bone cement is degassed during extrusion through the dispensing plunger.

Moreover, the invention can prevent the monomer liquid container from being opened in step (A) by pushing or screwing an opening facility into the receptacle.

This makes the method particularly easy to implement for the user. Moreover, a defined force for opening of the monomer liquid container can be provided, and reproducible opening of the monomer liquid container can thus be attained.

In this context, the invention can provide the monomer liquid container in step (A) to be pushed onto a mandrel on the inside of the receptacle and the receptacle to thus be opened, whereby the monomer liquid container preferably is an ampoule made of glass or a plastic material and the ampoule is opened by the mandrel at an ampoule base of the ampoule.

This also serves for opening the monomer liquid container at a defined place and to thus render the process of opening the monomer liquid container reproducible.

In this context, the mandrel can be pushed into the receptacle by the mixing rod or the mixing rod can puncture the mandrel and can be pushed through the mandrel into the receptacle in step (E).

This ensures that the mixing rod can be pushed without resistance through the opened monomer liquid container or through its fragments into the receptacle and into the opened monomer liquid container.

Moreover, the receptacle can be moved linearly in step (B) and can be screwed into the cartridge in steps (C) and (E), whereby the linear motion in step (A) is limited by a thread on the receptacle as a limit stop, whereby the thread is used to screw the receptacle into the cartridge in steps (C) and (E).

This can prevent the mixing rod from being detached from the receptacle during the mixing process. Moreover, it prevents a large force from being exerted on the closure of the dispensing opening during the mixing process, and prevents bone cement from exiting from the cartridge before the mixing process is completed. Moreover, the bone cement can thus be forcefully expelled from the internal space of the cartridge by the screw-type process.

Preferred embodiments of the method according to the invention can provide the inside of the receptacle to be connected in a gas-permeable manner to the surroundings of the bone cement applicator before step (A), whereby the inside of the receptacle is closed before step (A) or during step (A), while the monomer liquid container is being opened.

This allows the inside of the receptacle and the internal space of the cartridge, i.e., the entire bone cement applicator including its contents, to be sterilized by a sterilizing gas, such as ethylene oxide. Concurrently, the monomer liquid cannot exit from the receptacle once the monomer liquid container has been opened inside the receptacle.

The invention can just as well provide the bone cement applicator to be held or set up with the cartridge head facing downwards before step (A), whereby the cartridge head preferably stays oriented downwards during steps (A) and (B) such that the monomer liquid flows into the internal space of the cartridge driven by gravity.

By this design, no additional pump is required in order to transfer the monomer liquid into the internal space of the cartridge to the bone cement powder.

Moreover, the invention can provide any still remaining part of the monomer liquid to be pushed into the internal space of the cartridge during the insertion of the receptacle into the internal space of the cartridge during step (B).

What this attains is that the monomer liquid is transferred as completely as possible into the bone cement powder in order to attain the desired mixing ratio of bone cement powder and monomer liquid and to thus generate a bone cement with the desired properties.

Moreover, the invention can just as well provide the receptacle to be inserted fully into the internal space of the cartridge before step (C), such that the mixer touches against the cartridge head in the internal space of the cartridge, whereby the mixing rod is detached from the receptacle in step (C) and is being pushed into the receptacle in step (E) by the receptacle being pushed or screwed further into the cartridge.

By this feature, the mixing rod can be detached from the receptacle in a simple and forceful manner.

Lastly, the invention can provide a ring with a thread to be arranged on the rear side of the cartridge and can provide the receptacle to comprise a matching counter thread, whereby, after step (B) and before step (C), the ring is pushed or screwed in the axial direction with respect to the cylindrical internal space of the cartridge away from the cartridge head, such that the counter thread of the receptacle engages the thread of the ring, and, during steps (C) and (E), the receptacle is screwed into the thread of the ring and, in the process, the receptacle is moved in the internal space of the cartridge in the direction of the cartridge head, such that, in step (C), the mixing rod that touches against the internal side of the cartridge head is detached from the receptacle and, in step (E), the detached mixing rod is pushed into the receptacle and the dispensing plunger is pushed in the direction of the cartridge head by the front side of the receptacle.

As a result, the advantages specified above referring to the bone cement applicator with the ring are attained.

The invention is based on finding, surprisingly, that providing a mixing rod that can be detached from the receptacle and a mixing rod that can be retracted into the receptacle allows a bone cement applicator to be provided, in which the mixing rod does not need to be pulled out of the bone cement applicator and in which the mixing rod does not need to be broken off and removed, when the bone cement is dispensed with the bone cement applicator. Surprisingly, the receptacle, in which the monomer liquid container is arranged, can be used to accommodate the mixing rod. As a result, the mixing rod does not impede the motion of the dispensing plunger during extrusion of the bone cement. Moreover, because the receptacle is moved in the rear-side part of the internal space, it is an option to use the front side of the receptacle as the dispensing plunger or to at least drive the dispensing plunger directly with the receptacle. As a result, an axial motion of the receptacle can be used both for mixing the bone cement in the internal space of the cartridge and for expelling the bone cement and/or for driving the dispensing plunger.

Once the monomer liquid container is opened, the mixing rod is pushed into the hollow monomer liquid container inside the receptacle that has been emptied of monomer liquid, because the mixing rod and the monomer liquid container are arranged in succession in the bone cement applicator. The bone cement applicator according to the invention is a prepack mixing system and can be operated without prior assembly steps. No external vacuum source is required for the monomer transfer. The dispensation of the bone cement takes place through a manual screw motion of the hollow cylinder-shaped receptacle that forms a dispensing plunger on its front side that faces the cartridge head or drives the dispensing plunger in the internal space of the cartridge. The screw motion develops a sufficient extrusion force to be able to extrude even a high viscosity bone cement out of the cartridge and also for detaching the mixing rod from the receptacle. The components of the bone cement applicator can essentially be produced by plastic injection molding and preferably consist of inexpensive thermoplastic material. The O rings consist of elastomers that are common in medical technology, such as silicone or EPDM (terpolymers of ethylene, propylene, and a diene).

An exemplary bone cement applicator according to the invention designed for storage, mixing, and application, is composed of:

(a) a hollow cylinder-shaped cartridge, whereby a fastener for a cartridge lid (as a cartridge head) is arranged on a front end of the cartridge, and whereby an internal thread is arranged on the internal wall of the cartridge on the opposite rear-side end of the cartridge;

(b) a cartridge lid to be connected by the fastener to the front end of the cartridge in a gas-tight and liquid-tight manner, whereby the cartridge lid possesses a dispensing opening;

(c) a closure stopper that is arranged in the dispensing opening of the cartridge lid in a gas-tight and detachable manner;

(d) a hollow cylinder-shaped ampoule holder as a receptacle that possesses an external thread at its jacket surface, at least in a first section, and possesses no thread in a second section;

(e) a closure on the front side of the ampoule holder that closes the hollow cylinder-shaped ampoule holder on a longitudinal side, whereby a mixing rod with a mixer is attached in a detachable manner on the side of the closure that faces the cartridge head, and whereby the opposite side of the closure is connected to a mandrel;

(f) a dispensing plunger that can be shifted axially in the cartridge and is permeable to gases and liquids and is impermeable to bone cement powder particles and is arranged between the mixer and the closure of the ampoule holder in the cartridge;

(g) a monomer liquid container containing monomer liquid whose base side is arranged at a distance above the mandrel in the ampoule holder;

(h) a shiftable sleeve as part of an opening facility that is arranged above the monomer liquid container in the hollow cylinder-shaped ampoule holder so as to be shifted axially in an appropriate way, such that the opening facility with the sleeve projects beyond the edge of the hollow cylinder-shaped ampoule holder;

(i) a hollow closure cap of the hollow cylinder-shaped ampoule holder that is closed on one side, whereby an internal thread and a limit stop for the hollow cylinder-shaped ampoule holder are arranged in the hollow closure cap, whereby the distance between the lower external edge of the closure cap and the limit stop is preferred to be smaller than the distance between the external end of the sleeve and the edge of the narrow side of the ampoule holder from which the sleeve projects;

(j) optionally, at least one ventilation opening in the jacket surface of the hollow cylinder-shaped ampoule holder, whereby the ventilation opening can be closed in a gas-tight manner by shifting the sleeve axially;

(k) bone cement powder that is arranged in a front part of the internal space of the cartridge that is formed by the internal wall of the cartridge, the cartridge lid, and the dispensing plunger;

(l) whereby the hollow cylinder-shaped ampoule holder is or can be screwed to the internal thread of the cartridge by its external thread; and (m) at least the mixing rod can be shifted into the hollow space of the ampoule holder or of the monomer liquid container after the monomer liquid container has been opened.

It is advantageous to have the closure with the mixing rod and the mandrel be designed as a single part. This clearly reduces the assembly effort as compared to a two-part or three-part closure with mixing rod and mandrel. The one-part closure with mixing rod and mandrel can advantageously be manufactured by plastic injection molding.

The invention can just as well provide the closure to be affixed in a detachable manner in the hollow cylinder-shaped ampoule holder through a press-fit. In this context, the closure can be conical and can be supported in a conical seat of the hollow cylinder-shaped ampoule holder. The cone of the closure tapers in the direction of the cartridge head. Upon a motion of the hollow cylinder-shaped ampoule holder in the direction of the cartridge head, the mixing rod with mixing elements braces on the internal side of the cartridge lid and pushes the conical closure out of its seat. The mandrel with the closure and the mixing rod then enter the inside of the ampoule holder and the opened monomer liquid container.

In another implementation variant, an internal part of the closure in the hollow cylinder-shaped ampoule holder has an external thread that is screwed into an internal thread of the hollow cylinder-shaped ampoule holder, whereby the internal part of the closure preferably possesses a left-hand external thread. When the hollow cylinder-shaped ampoule holder is rotated, it moves in the direction of the cartridge head. The mixing rod with the mixing elements is pressed to the inside of the lid. With increasing contact pressure against the lid, the mixing rod can no longer rotate along with the ampoule holder. The internal part of the closure is then rotated out of the internal thread of the hollow cylinder-shaped ampoule holder. The internal part of the closure leaves its seat in the hollow cylinder-shaped ampoule holder and is pushed, together with the mandrel and the mixing rod, into the opened monomer liquid container.

In another implementation variant, the mixing rod is pressed into the closure and penetrates through the closure and the mandrel after the monomer liquid container has been opened. Then, the mixing rod is inserted into the ampoule holder.

The invention can just as well provide the hollow cylinder-shaped ampoule holder to have a diameter at its cylinder-shaped head side that is equal to or smaller than the internal diameter of the hollow cylinder-shaped cartridge, and can provide the hollow cylinder-shaped ampoule holder to be axially movable in the cartridge by its head side in a gas-tight manner.

Moreover, the sleeve can be designed as a hollow cylinder, whereby the cylinder jacket of the sleeve rests on the monomer liquid container, and whereby the sleeve is closed by a gas-tight separating wall on the inside of the hollow space or on the end of the sleeve.

Moreover, the internal part of the closure can have an external diameter that is smaller than the internal diameter of the monomer liquid container. By this design, the internal part of the closure with the mandrel and the mixing rod can be readily pushed into the inside of the opened monomer liquid container.

An exemplary method according to the invention for the mixing and application of polymethylmethacrylate bone cement using a bone cement applicator according to the invention can be implemented through the following steps proceeding in the order given:

(a) positioning the bone cement applicator vertically with the cartridge head downwards;
(b) screwing the closure cap, which is screwed onto the hollow cylinder-shaped ampoule holder as a receptacle, in the direction of the cartridge head;
(c) shifting the sleeve in the direction of the cartridge head using the closure cap;
(d) optionally, closing the at least one gas supply opening in the hollow cylinder-shaped ampoule holder using the sleeve;
(e) shifting the monomer liquid container in the direction of the mandrel by shifting the sleeve axially;
(f) destroying the base of the monomer liquid container by the mandrel;
(g) flowing monomer liquid out through the closure and the dispensing plunger, which is permeable to gases and liquids, into the internal space of the cartridge to the bone cement powder;
(h) retracting the hollow cylinder-shaped ampoule holder opposite to the cartridge head during a concurrent backward motion of the mixing rod while mixing the bone cement powder and the monomer liquid;
(i) moving the ampoule holder forward, transferring the remaining monomer liquid, through the overpressure over the monomer liquid, through the closure and the dispensing plunger, which is permeable to gases and liquids, during a concurrent backward motion of the mixing rod while mixing the bone cement powder and the monomer liquid;
(j) multiply repeating steps (h) and (i);
(k) producing the bone cement from the mixture of polymethylmethacrylate bone cement powder and monomer liquid;
(l) removing the closure stopper from the dispensing opening;
(m) screwing the hollow cylinder-shaped ampoule holder in the direction of the cartridge head, whereby the mixing rod with the mixing elements lands on the internal side of the lid (of the cartridge head) and pushes the internal part of the closure out of its conical seat in the hollow cylinder-shaped ampoule holder in the direction of the cartridge base;
(n) inserting the closure with the mandrel and mixing rod into the opened monomer liquid container; and
(o) extruding the polymethylmethacrylate bone cement in the direction of the cartridge head through the screw motion of the ampoule holder.

An exemplary alternative method for the mixing and application of polymethylmethacrylate bone cement using the bone cement applicator according to the invention can be characterized by the following steps proceeding in the order given:

(a) positioning the bone cement applicator vertically with the cartridge head downwards;
(b) screwing the closure cap, which is screwed onto the hollow cylinder-shaped ampoule holder as the receptacle, in the direction of the cartridge head;
(c) shifting the sleeve in the direction of the cartridge head using the closure cap;
(d) closing the at least one gas supply opening in the hollow cylinder-shaped ampoule holder using the sleeve;
(e) shifting the monomer liquid container in the direction of the mandrel by shifting the sleeve axially;
(f) destroying the base of the monomer liquid container by the mandrel;
(g) flowing monomer liquid out through the closure and the dispensing plunger, which is permeable to gases and liquids, into the front part of the internal space of the cartridge to the bone cement powder;
(h) retracting the hollow cylinder-shaped ampoule holder opposite to the cartridge head during a concurrent backward motion of the mixing rod while mixing the bone cement powder and the monomer liquid;
(i) moving the ampoule holder forward, transferring the remaining monomer liquid, through the overpressure over the monomer liquid, through the closure and the dispensing plunger, which is permeable to gases and liquids, during a concurrent backward motion of the mixing rod while mixing the bone cement powder and the monomer liquid;
(j) multiply repeating steps (h) and (i);
(k) producing the bone cement from the mixture of polymethylmethacrylate bone cement powder and monomer liquid;
(l) removing the closure stopper from the dispensing opening;
(m) screwing the hollow cylinder-shaped ampoule holder in the direction of the cartridge head, whereby the mixing rod with the mixing elements lands on the internal side of the lid and unscrews the external thread of the internal part of the closure from the internal thread of the hollow cylinder-shaped ampoule holder in the direction of the cartridge base;
(n) inserting the closure with the mandrel and mixing rod into the opened monomer liquid container; and
(o) extruding the polymethylmethacrylate bone cement in the direction of the cartridge head through the screw motion of the ampoule holder.

Another exemplary alternative method for the mixing and application of polymethylmethacrylate bone cement using the bone cement applicator according to the invention can be characterized by the following steps proceeding in the order given:

(a) positioning the bone cement applicator vertically with the cartridge head downwards;

(b) screwing the closure cap, which is screwed onto the hollow cylinder-shaped receptacle, in the direction of the cartridge head;

(c) shifting the sleeve in the direction of the cartridge head using the closure cap;

(d) closing the at least one gas supply opening in the hollow cylinder-shaped receptacle using the sleeve;

(e) shifting the monomer liquid container in the direction of the mandrel by shifting the sleeve axially;

(f) destroying the base of the monomer liquid container by the mandrel;

(g) flowing monomer liquid out through the closure and the dispensing plunger, which is permeable to gases and liquids, into the front part of the internal space of the cartridge to the bone cement powder;

(h) retracting the hollow cylinder-shaped receptacle opposite to the cartridge head during a concurrent backward motion of the mixing rod while mixing the bone cement powder and the monomer liquid;

(i) moving the receptacle forward, transferring the remaining monomer liquid, through the overpressure over the monomer liquid, through the closure and the dispensing plunger, which is permeable to gases and liquids, during concurrent backward motion of the mixing rod while mixing the bone cement powder and the monomer liquid;

(j) multiply repeating steps (h) and (i);

(k) producing the bone cement from the mixture of polymethylmethacrylate bone cement powder and monomer liquid;

(l) removing the closure stopper from the dispensing opening;

(m) screwing the hollow cylinder-shaped receptacle in the direction of the cartridge head, whereby the mixing rod with the mixing elements lands on the internal side of the lid and punctures the closure and the mandrel;

(n) inserting the mixing rod into the opened monomer liquid container; and (o) extruding the polymethylmethacrylate bone cement in the direction of the cartridge head through the screw motion of the receptacle.

The extrusion of the bone cement takes place by driving the dispensing plunger with the receptacle and/or with the ampoule holder.

BRIEF DESCRIPTION OF THE DRAWING

The disclosure is best understood from the following detailed description when read in connection with the accompanying drawing. Further exemplary embodiments of the invention are explained below with reference to twelve schematic figures, although without limiting the scope of the invention. In the figures.

DETAILED DESCRIPTION OF THE DISCLOSURE

Figure 1:
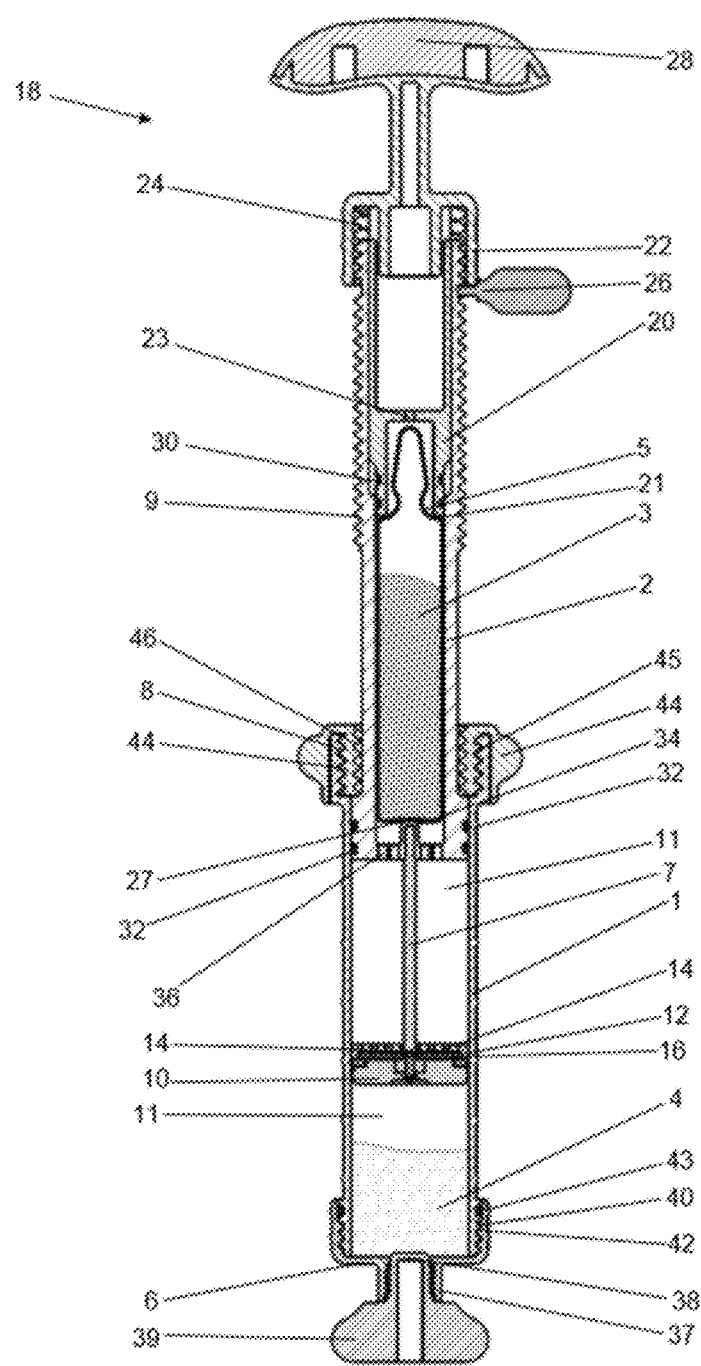
FIG. 1 is a schematic cross-sectional view of a first exemplary bone cement applicator according to the invention for the production of a bone cement dough.
Figure 2:
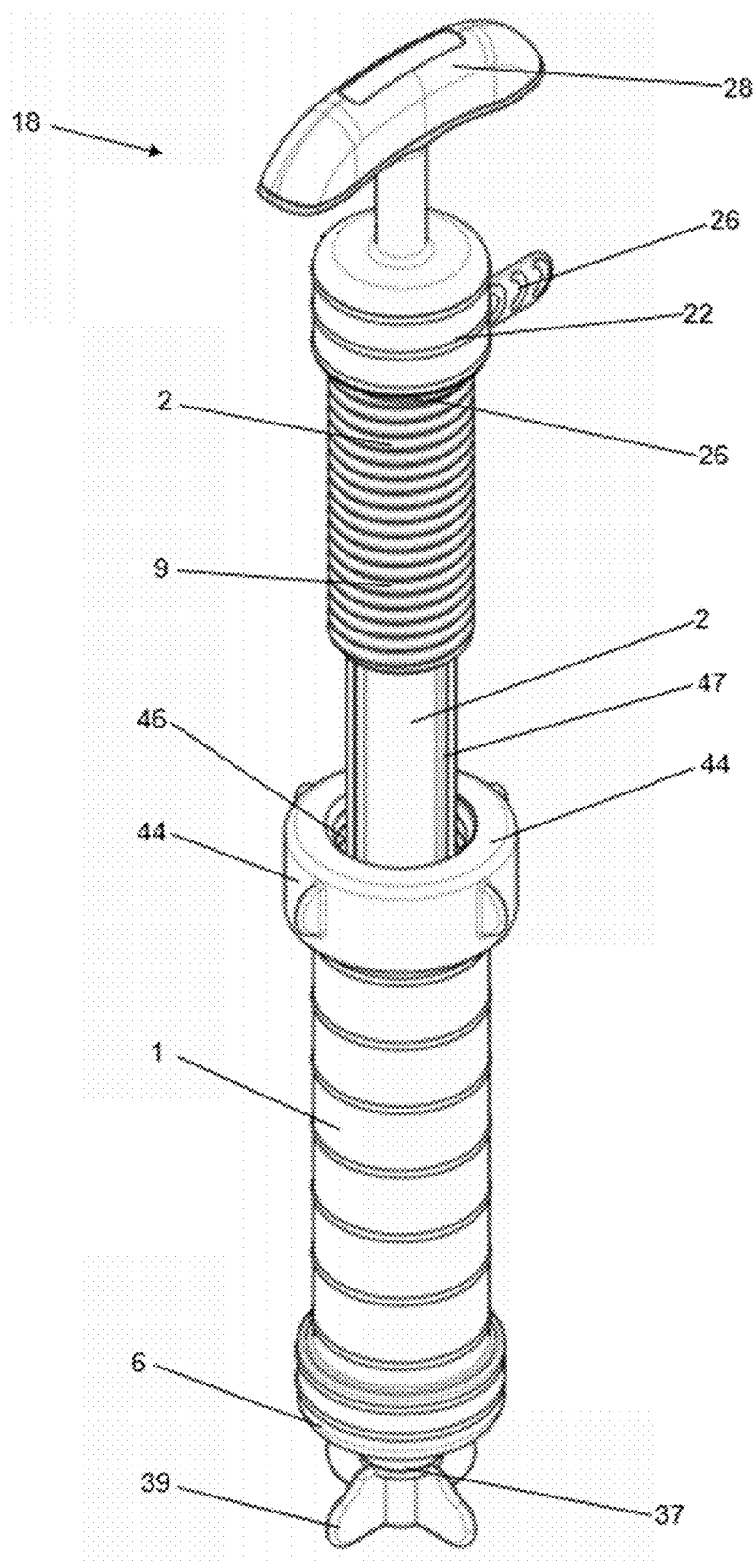
FIG. 2 is a schematic perspective external view of the first bone cement applicator according to the invention as shown in FIG. 1.
Figure 3:
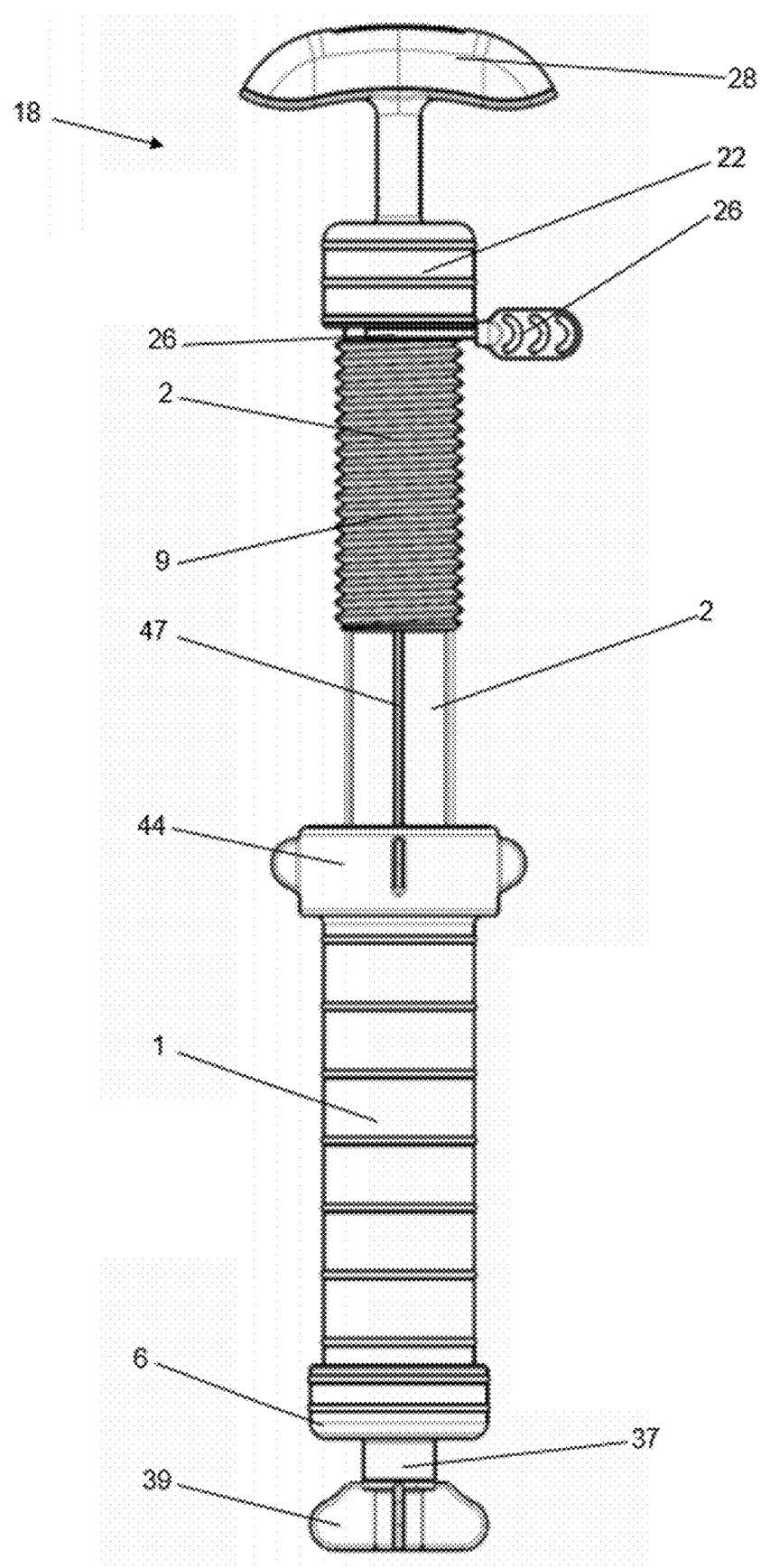
FIG. 3 is a schematic side view of the first bone cement applicator according to the invention as shown in FIGS. 1 and 2.

FIGS. 1 to 6 depict a first bone cement applicator for the storage of starting components 3, 4 of a bone cement 48 and for the mixing of the bone cement 48. In this context, FIGS. 1 and 4 to 6 show the work-flow of a method that is implemented using the first bone cement applicator in the form of four cross-sectional views of the first bone cement applicator.

The first bone cement applicator comprises a tube-shaped cartridge 1 made of plastic that forms a front part (on the bottom in FIGS. 1 to 6) of the bone cement applicator. A rear-side rear part of the bone cement applicator is formed by a receptacle 2. The bone cement applicator is intended for the production of a bone cement 48 (see FIGS. 5 and 6) that is produced from a monomer liquid 3 and from a bone cement powder 4. The monomer liquid 3 and the bone cement powder 4 are the starting components 3, 4 of the bone cement 48. The monomer liquid 3 is contained in an ampoule 5 that can be fractured and is made of glass or a plastic material as the monomer liquid container for the monomer liquid 3, whereby the ampoule 5 is plugged into the receptacle 2. The cartridge 1 forms a cylindrical internal space 11 on its inside that contains the bone cement powder 4. Accordingly, the bone cement applicator is also well-suited for storage of the monomer liquid 3 and bone cement powder 4.

The cartridge 1 comprises a cartridge lid 6 as a cartridge head on its front side (on the bottom in the figures). A dispensing opening is provided in the cartridge lid 6. According to an alternative variant of the bone cement applicator, multiple gas supply openings (not shown) through which a gas can be aspirated from the inside of the bone cement applicator and through which a sterilizing gas such as ethylene oxide can be delivered for sterilization of the inside of the bone cement applicator can be situated in the side wall of the receptacle 2.

A mixing rod 7 is fastened to the front side of the receptacle 2 and extends from the front side of the receptacle 2 up into the front part of the cartridge 1, in which the bone cement powder 4 is situated.

An internal thread 8 is situated on the rear-side end of the cartridge 1. The receptacle 2 comprises, on its outside, an external thread 9 with a diameter that is smaller than that of the internal thread 8 of the cartridge 1. The receptacle 2 is shaped, in a rear region, in the way of a threaded tube and comprises, on its inside, a cylindrical chamber into which the ampoule 5 is plugged. In a front area, the receptacle 2 is cylinder-shaped on its outside, whereby four projecting strips 47 are provided on the external surface of the receptacle 2 parallel to the cylinder axis of the receptacle 2. The ampoule 5 has a cylindrical ampoule body with a diameter that matches the inside of the receptacle 2. On the inside of the cartridge 1, the cartridge 1 forms the cylindrical internal space 11. The cylinder geometry of the internal space 11 and of the chamber of the receptacle 2 corresponds to cylinders with a circular footprint.

A mixer 10 is fastened to the front side of the mixing rod 7 in the form of mixing vanes with a surrounding scraping ring. The presence of a scraping ring allows the areas right at the internal wall of the internal space 11 to be reached.

The receptacle 2 is bordered on its front side by a wall with multiple passages 36 as a closure of the front side, whereby the wall on the front side of the receptacle 2 closes the chamber toward the front at its circular base surface. A dispensing plunger 12 is arranged in the internal space 11 of the cartridge 1 so as to be mobile in the axial direction of the cylindrical internal space 11, and is arranged in the internal space 11 in a press-fit. The mixing rod 7 is guided through a central passage in the dispensing plunger 12 such that the mixing rod 7 can be moved against the dispensing plunger 12 without the dispensing plunger 12 moving in the internal space 11 of the cartridge 1 in this context. With the receptacle 2 retracted, the mixer 10 touches against the front side of the dispensing plunger 12. As a result, the mixer 10 can reach the entire front part of the internal space 11 that is bordered on the side by the cartridge 1, on the front by the cartridge lid 6, and in the rear by the dispensing plunger 12. As a result, complete mixing of the bone cement powder 4 with the monomer liquid 3 in this area is ensured.

The dispensing plunger 12 comprises multiple channels 14 passing through the dispensing plunger 12, which are arranged in a ring shape about the central passage for the mixing rod 7 in the dispensing plunger 12 and connect the front side of the dispensing plunger 12 to the rear side of the dispensing plunger 12 and thereby connect the two sides of the internal space 11 of the cartridge 1 to each other. The channels 14 are covered by a ring-shaped pore filter 16. The pore filter 16 is impermeable to the bone cement powder 4 from the internal space 11 of the cartridge 1, and is permeable to the monomer liquid 3 and gases. As a result, the bone cement powder 4 is prevented from ingress into the inside of the receptacle 2.

The dispensing plunger 12 comprises a larger external diameter than the external thread 9 of the receptacle 2. The external diameter of the cylindrical dispensing plunger 12 fits the internal diameter of the internal space 11 of the cartridge 1. The dispensing plunger 12 seals the internal space 11 of the cartridge 1.

An opening facility 18 is provided on the rear side of the receptacle 2 and can be used to push the ampoule 5 in the direction of the dispensing plunger 12 in order to open the ampoule 5 on the inside of the receptacle 2 such that the monomer liquid 3 in the receptacle 2 flows out. For this purpose, the opening facility 18 comprises a two-step sleeve 20, whereby the front side of the sleeve 20 forms a hollow cylinder in which an ampoule head of the ampoule 5 is arranged. The sleeve 20 of the opening facility 18 can thus push onto shoulders 21 of the ampoule 5 in order to push the ampoule 5 to the front in the direction of the dispensing plunger 12 and to thus open it. Because the sleeve 20 presses onto the shoulders 21, the force is guided through the ampoule body to an ampoule base 27 of the ampoule 5. The walls of the ampoule body are very stable such that the ampoule 5 will not fracture in this area. The ampoule 5 can thus be fractured at the ampoule base 27.

In this context, the sleeve 20 touches against the internal wall of the receptacle 2 and covers it in the area of the rear side of the inside of the receptacle 2. The rear-side end of the receptacle 2 is covered by a closure cap 22 of the opening facility 18. A wall perpendicular to the axis of the cylinder geometry of the sleeve 20 is provided in the sleeve 20, whereby an opening 23 is provided in the wall. The opening 23 prevents a gas spring from being formed during the insertion of the receptacle 2 into the cartridge 1. Moreover, the monomer liquid 3 can flow more easily out of the receptacle 2 if air can flow through the opening 23. For application, the bone cement applicator needs to be held or set up with the cartridge lid 6 facing downwards, as is shown in FIGS. 1 to 6. The sleeve 20 is fastened to the screw-type closure cap 22. The closure cap 22 comprises an internal thread 24 that fits the external thread 9 of the receptacle 2.

The closure cap 22, or the opening facility 18 as it may be, is screwed a way, but not all the way to a limit stop, onto the rear side of the receptacle 2 and is thus fastened to the receptacle 2. It is important that the closure cap 22 can be screwed further onto the receptacle 2 and that the sleeve 20 can be inserted more deeply into the receptacle 2 by this configuration to allow the ampoule 5 to be opened in the receptacle 2.

On the rear side of the receptacle 2, a circumferential groove is provided in the external thread 9, into which a securing element 26 in the form of a brace is plugged. The securing element 26 prevents the closure cap 22 from being screwed onto the receptacle 2 inadvertently and thus prevents the opening facility 18 from being operated inadvertently. The securing element 26 can be detached right before a use of the bone cement applicator by pulling off the securing element 26. The opening facility 18 can then be screwed into the receptacle 2.

In order to prevent the closure cap 22 from rotating in the wrong direction and thus to prevent the receptacle 2 from being opened on its rear side, a reverse motion lock is provided (not shown in FIGS. 1 to 6). The reverse motion lock prevents the closure cap 22 from detaching and/or the opening facility 18 from detaching from the receptacle 2. The reverse motion lock can be implemented, for example, as a screw lock in the form of a locking disk or by a pair of wedge lock disks or similar measures.

In order to be able to conveniently rotate the opening facility 18 and the receptacle 2 by hand and in order to be able to conveniently insert and pull out the receptacle 2 into and out of the cartridge 1, the rear-side end thereof is fitted with a handle 28. For sealing the sleeve 20 with respect to the internal wall of the receptacle 2, two circumferential seals 30 made of rubber are arranged in circumferential grooves on the front-most external circumference of the sleeve 20. The sleeve 20 is graduated on the outside and thus forms a limit stop in addition to the limit stop formed by the closure cap 22, whereby the limit stops prevent the opening facility 18 from being screwed further onto and/or into the receptacle 2.

Likewise, the external circumference of the dispensing plunger 12 has two grooves arranged on it, in which two circumferential seals 32 made of rubber are situated and which are situated at a distance from each other in the longitudinal direction. The seals 32 seal the dispensing plunger 12 with respect to the internal space 11 of the cartridge 1 and separate the internal space 11 of the cartridge 1 into a front part, in which the bone cement powder 4 is arranged, and a rear part.

A mandrel 34 for fracturing the ampoule 5 is arranged on the front wall of the receptacle 2 that points to the cartridge lid 6. For this purpose, the mandrel 34 points into the inside of the receptacle 2. In order to open the ampoule 5, the ampoule 5 can be pushed, by the sleeve 20, onto the mandrel 34 until the ampoule base 27 of the ampoule 5 is pushed into the ampoule body. The mandrel 34 has a blunt tip whose purpose is to have the force act on the ampoule 5 on a middle area of the ampoule base 27 such that a predetermined breakage site in the connection between the ampoule base 27 and the side walls of the ampoule body is used. The force for this purpose is exerted via the sleeve 20. The sleeve 20 has approximately the same diameter as the ampoule body of the ampoule 5. The ampoule head of the ampoule 5 is arranged on the inside of the sleeve 20 in this context. What this attains is that the ampoule 5 is not fractured in the area of the sleeve 20, because the cylindrical ampoule body is very stable, whereas the mandrel 34 can be pushed relatively easily from the front into the ampoule 5.

The mixing rod 7 is fastened to the receptacle 2 inside the mandrel 34. The mandrel 34 is connected to the receptacle 2 by a predetermined breakage site such that a pressure being exerted on the mixing rod 7 causes the mixing rod 7 to sever the mandrel 34 from the receptacle 2 such that the mixing rod 7 with the mandrel 34 at the tip can be moved through the front base surface of the receptacle 2. Alternatively, an internal circular disk (not shown) of the front side of the receptacle 2 can be connected to the receptacle 2 by a thread such that the mandrel 34 can be separated, by the circular disk, from the remaining receptacle 2 by a rotation of the receptacle 2 against the mixing rod 7, which is affixed to the cartridge lid 6 for this purpose such that the mixing rod 7 again can be moved with respect to the remaining receptacle 2.

Figure 4:
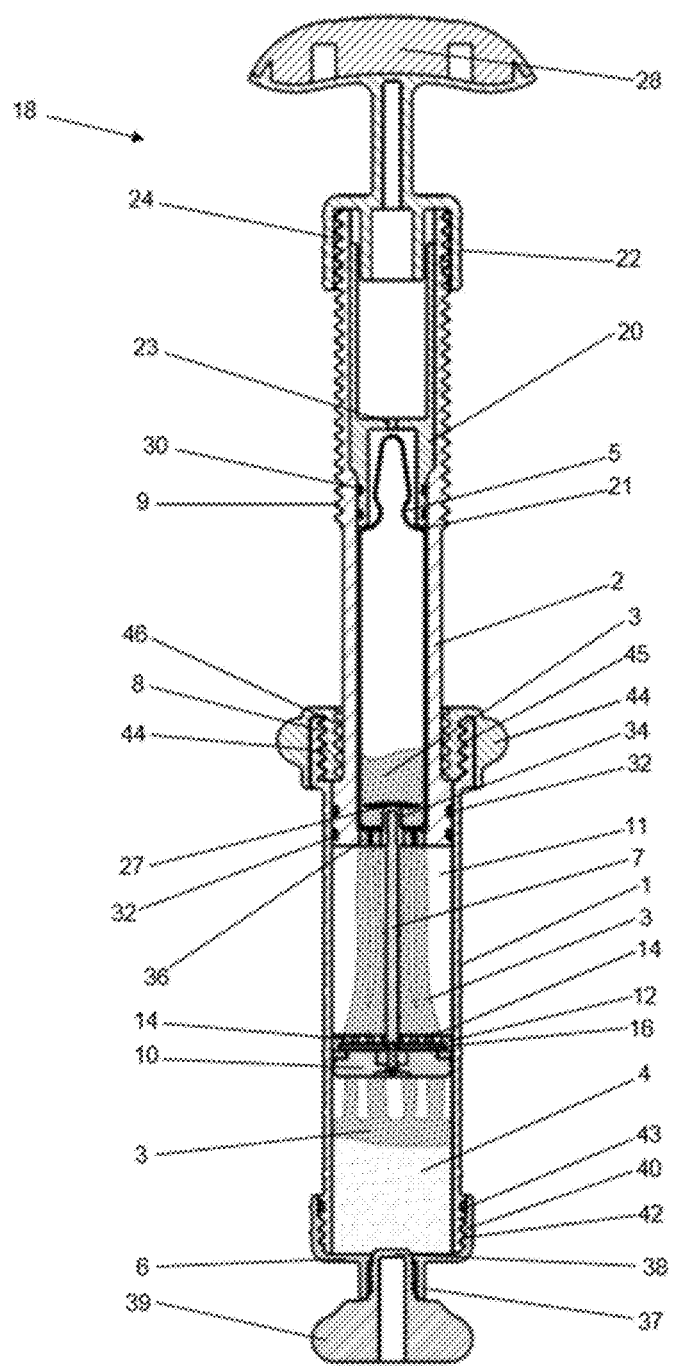
FIG. 4 is a schematic cross-sectional view of the first bone cement applicator according to the invention as shown in FIGS. 1 to 3 having an opened monomer liquid container for illustration of the work-flow of a method according to the invention.

Multiple passages 36 are arranged about the mandrel 34 and connect the inside of the receptacle 1 to the internal space 11 of the cartridge 1. The monomer liquid 3 can flow through the passages 36 into the internal space 11 of the cartridge 1, as is shown in FIG. 4.

The front side of the cartridge 1 is closed by the cartridge lid 6. A socket 37 bordering the dispensing opening in the cartridge lid 6 is formed in the middle of the cartridge lid 6. A closure 38 for closing the dispensing opening is screwed into the socket 37 and is thus fastened in a detachable manner. The closure 38 can be operated via wings 39 in the way of a wing screw. The cartridge lid 6 is screwed onto an external thread 42 on the front side of the cartridge 1 by an internal thread 40. The cartridge lid 6 is additionally sealed with respect to the cartridge 1 by a circumferential seal 43.

The front part of the internal space 11 of the cartridge 1 has the mixer 10 arranged in it, by which the content of the front part of the internal space 11 can be mixed through a manual motion of the mixer 10. The manual motion of the mixer 10 takes place by inserting and pulling out the receptacle 2 into and from the cartridge 1. Namely, this action also causes the mixing rod 7, which is fastened to the front side of the receptacle 2, to be moved back and forth in a linear manner. In this context, the mixing rod 7 moves through the feedthrough in the dispensing plunger 12, and the mixer 10 fastened to the mixing rod 7 moves in the front part of the internal space 11 of the cartridge 1.

The internal thread 8 on the rear side of the cartridge 1 has a larger diameter than the internal space 11. A screw ring 44 with an external thread 45 that matches the internal thread 8 is screwed into the internal thread 8. The screw ring 44 has an internal thread 46 on its inside that matches the external thread 9 of the receptacle 2. Accordingly, the receptacle 2 can be screwed into the internal thread 46 of the screw ring 44 (see FIG. 6).

In addition, the internal thread 46 of the screw ring 44 serves as a limit stop for the insertion of the receptacle 2 into the cartridge 1. Namely, when the receptacle 2 is inserted into the cartridge 1 up to the limit stop, the external thread 9 of the receptacle 2 meets the internal thread 46 of the screw ring 44, which is fully screwed into the internal thread 8 on the rear side of the cartridge 1. Concurrently, the length of the mixing rod 7 is selected appropriately such that the mixer 10 touches against the cartridge lid 6 at the front side of the internal space 11. By this configuration, the bone cement 48 at the front side of the internal space 11 can also be reached and mixed by the mixer 10.

The closure 38 projects a little ways into the internal space 11 of the cartridge 1. A recess accommodating the part of the closure 38 that projects into the internal space 11 is provided on the front side of the mixer 10 that faces the cartridge lid 6. By this configuration, the bone cement 48 touching against the closure 38 and against the cartridge lid 6 can also be mixed, and having this recess also provides a free cross-section of flow to the bone cement 48, when the closure 38 is removed and the mixer 10 touches against the cartridge lid 6 during the dispensation of the bone cement 48 (see FIG. 6).

The work-flow of a method according to the invention is described in the following based on FIGS. 1 to 6. Initially, the bone cement applicator is in the starting state (see FIGS. 1 to 3). In this state, the bone cement applicator has been packaged and sterilized with ethylene oxide. The ethylene oxide can enter into the inside of the receptacle 2 through gaps in the opening facility 18 and through the opening 23 and can enter into the internal space 11 of the cartridge 1 through the passages 36, the pore filter 16, and the channels 14. The gas exchange takes place in a vacuum chamber or negative pressure chamber in this context. In this state (see FIGS. 1 to 3), the bone cement applicator is unpacked.

The securing element 26 is pulled off first. The bone cement applicator is held with the cartridge lid 6 downwards. Subsequently, the opening facility 18 is screwed into the receptacle 2. As before, the bone cement applicator is held with the cartridge lid 6 downwards. In this context, the sleeve 20 pushes the shoulders 21 of the ampoule 5 in a downward direction. Subsequently, the ampoule 5 is pushed onto the mandrel 34 by its ampoule base 27, and the ampoule 5 fractures at its ampoule base 27. This state is shown in FIG. 4.

The monomer liquid 3 exits from the opened ampoule 5 in the area of the passages 36. Because the bone cement applicator is held with the cartridge lid 6 downwards, the monomer liquid 3 driven by gravity immediately flows downwards through the passages 36, the pore filter 16, and the channels 14 into the internal space 11 of the cartridge 1 and distributes in the bone cement powder 4 (see FIG. 4). In order to accelerate the monomer transfer, the receptacle 2 can be pushed into and pulled out of the cartridge 1.

The mixing of the bone cement 48 and/or of the starting components 3, 4 of the bone cement 48 takes place by inserting and pulling out the receptacle 2 into and out of the cartridge 1, while the mixer 10 moves simultaneously in the internal space 11 of the cartridge 1. In this context, the mixer 10 reaches all spaces in the internal space 11 between the dispensing plunger 12 and the cartridge lid 6. To guide this motion, the strips 47 touching against the internal thread 46 of the screw ring 44 are arranged on the outside of the receptacle 2 in the front area with no external thread 9. The strips 47 prevent the receptacle 2 from wobbling during the mixing process. The gaps allow air to escape that would otherwise be enclosed between the screw ring 44, the external wall of the receptacle 2, the internal wall of the cartridge 1, and the seal 32. This configuration prevents having to work against the force of a gas spring in this area while the bone cement 48 and/or the starting components 3, 4 are being mixed.

Figure 5:
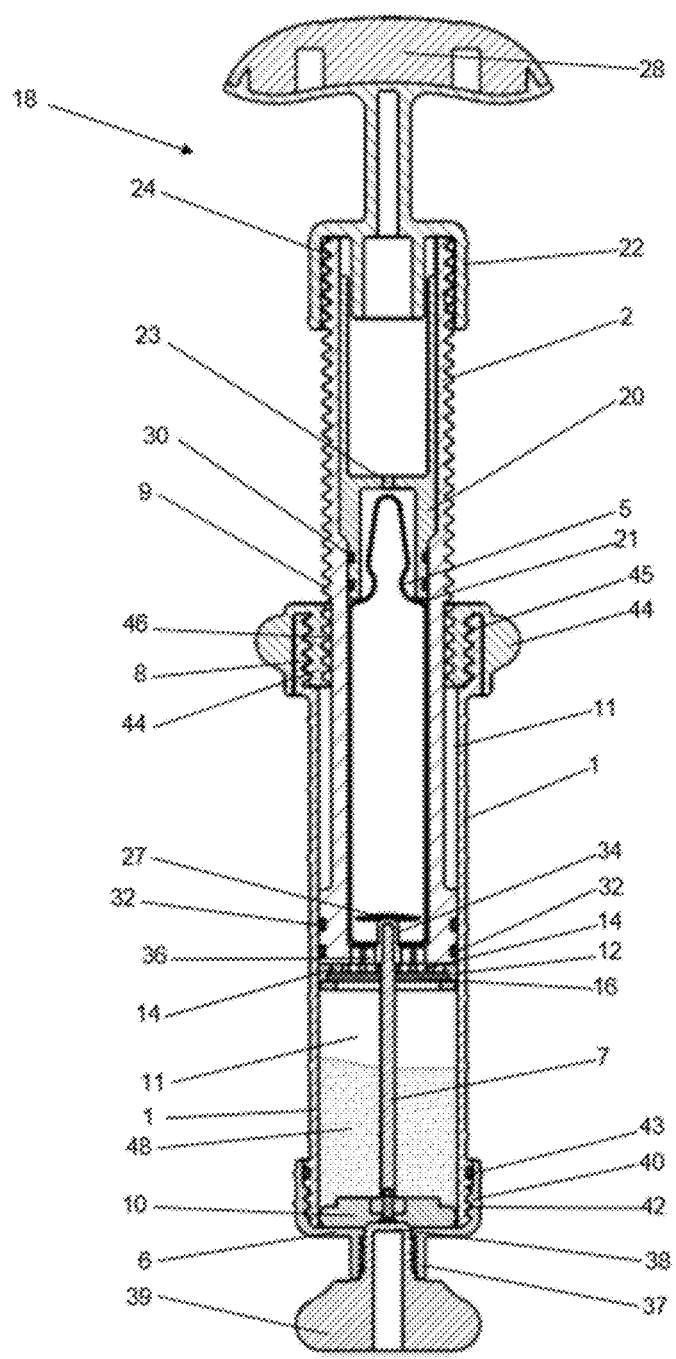
FIG. 5 is a schematic cross-sectional view of the first bone cement applicator according to the invention as shown in FIGS. 1 to 4 having the receptacle inserted into the cartridge for illustration of the work-flow of a method according to the invention.
Figure 6:
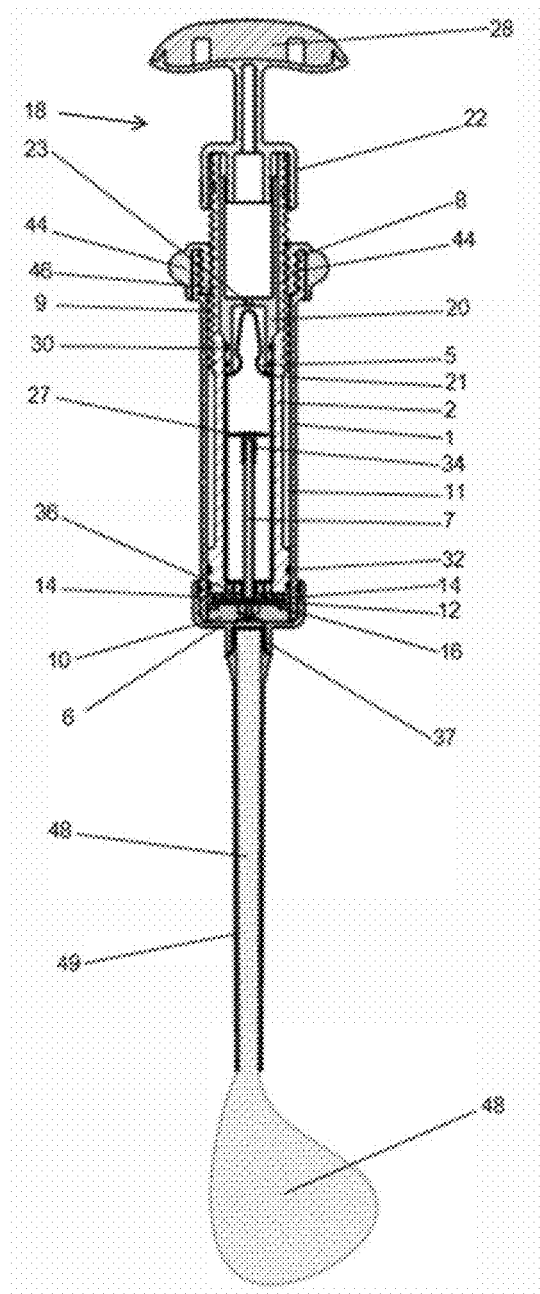
FIG. 6 is a schematic cross-sectional view of the first bone cement applicator according to the invention as shown in FIGS. 1 to 5 having the receptacle screwed into the cartridge after dispensation of the bone cement for illustration of the work-flow of a method according to the invention.
Figure 7:
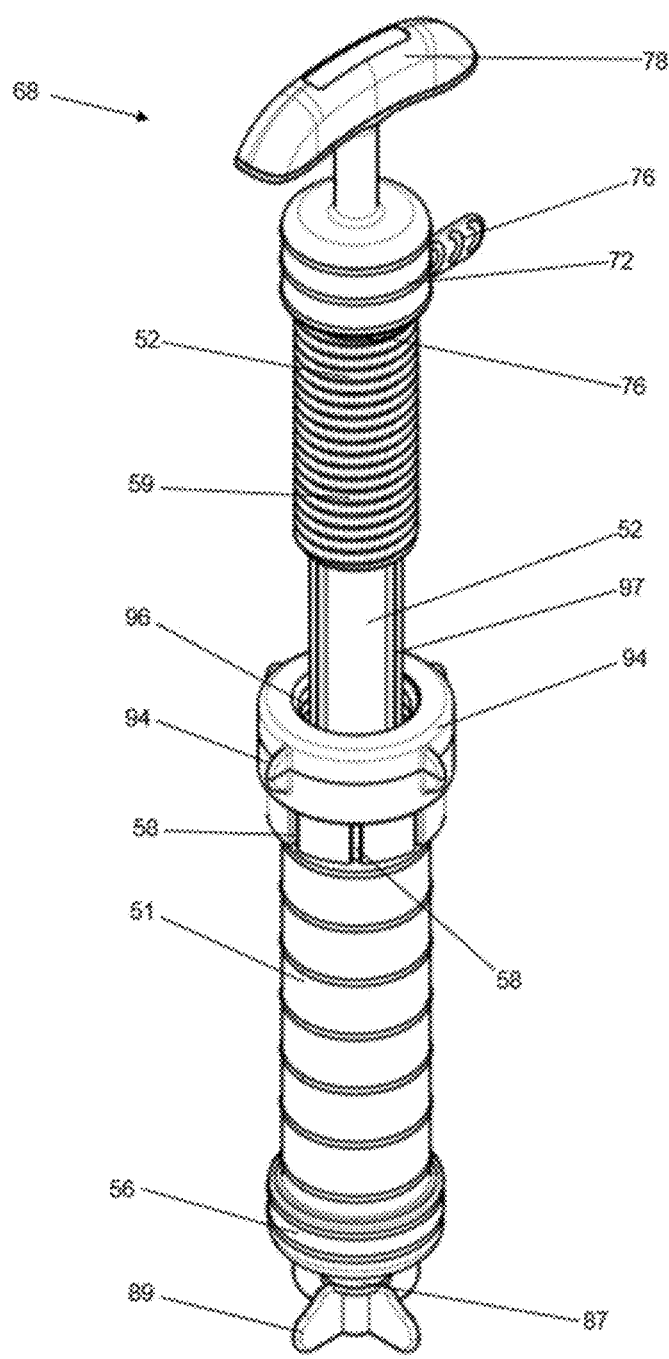
FIG. 7 is a schematic perspective external view of an exemplary second bone cement applicator according to the invention for the production of a bone cement dough.
Figure 8:
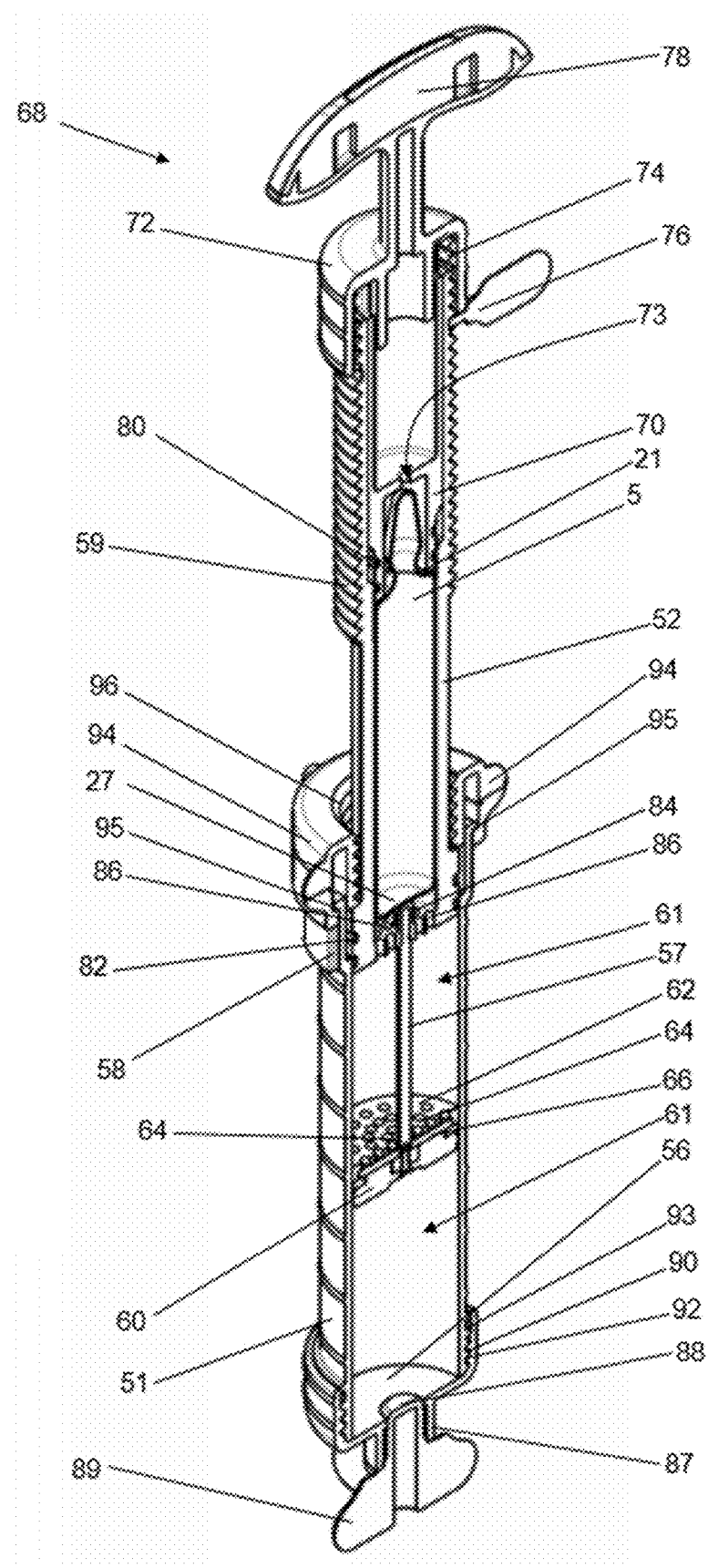
FIG. 8 is a schematic perspective cross-sectional view of the second bone cement applicator according to the invention as shown in FIGS. 1 to 7 without the starting components in the storage condition.

Finally, the bone cement 48 is successfully mixed and the receptacle 2 is inserted fully into the cartridge 1 such that the mixer 10 touches against the cartridge lid 6. This scenario is shown in FIG. 5.

In order to be able to screw the receptacle 2 into the internal thread 46 of the screw ring 44, the screw ring 44 needs to be unscrewed some way out of the internal thread 8 of the cartridge 1 after the bone cement 48 has been mixed. As a result, the internal thread 46 of the screw ring 44 can engage the external thread 9 of the receptacle 2. The screw ring 44 must not be detached completely from the cartridge 1 in this context. A suitable connector (not shown) can be provided for this purpose. By this configuration, the receptacle 2 can be screwed into the screw ring 44 and thus into the cartridge 1. As a result, the receptacle 2 can be pushed forcefully into the cartridge 1. The front of the mixer 10 touches against the cartridge lid 6 such that the mixing rod 7 cannot get out of the way. The pressure transmitted by the mixing rod 7 detaches the mandrel 34 from the front wall of the receptacle 2 or the mixing rod 7 punctures the mandrel 34. Concurrently, the dispensing plunger 12, which is supported in a press fit, is detached from the receptacle 2 and driven in the direction of the cartridge lid 6.

When the receptacle 2 is screwed further into the cartridge 1, the bone cement 48 is expelled out of the internal space 11 of the cartridge 1 through the opened dispensing opening. For this purpose, the closure 38 is first unscrewed from the dispensing opening and a dispensing tube 49 is screwed into the internal thread of the socket 37. For this purpose, the dispensing tube 49 has an external thread that matches the internal thread of the socket 37. The bone cement 48 is pressed between the mixer 10 and the cartridge lid 6, through the dispensing opening and the socket 37 into the dispensing tube 49. Subsequently, the bone cement 48 flows out of the dispensing tube 49 and is ready for application (see FIG. 6).

During the extrusion of the bone cement 48, gas inclusions in the bone cement 48 are pushed upwards into the receptacle 2 through the pore filter 16 such that a gas-depleted bone cement 48 is produced.

As an alternative to the dispensing tube 49, a hose with a trocar (not shown) can be fastened to the socket 37 through which the bone cement 48 can be applied under X-ray control in places that are difficult to access.

FIGS. 7 to 12 show depictions of a second alternative bone cement applicator for storage of the starting components 3, 4 of the bone cement 48 and for mixing of the bone cement 48. In this context, the figures also show the workflow of a method that is implemented using the second bone cement applicator in the form of five cross-sectional views of the second bone cement applicator.

The design of the second bone cement applicator is largely similar to that of the first bone cement applicator illustrated in FIGS. 1 to 6. The second bone cement applicator comprises a tube-shaped cartridge 51 made of plastic that forms a front part (on the bottom in FIGS. 7 to 12) of the bone cement applicator. A rear-side rear part of the bone cement applicator is formed by a receptacle 52. The bone cement applicator is intended for the production of the bone cement 48 (see FIGS. 11 and 12) that is produced from the monomer liquid 3 and from the bone cement powder 4. Accordingly, the starting components 3, 4 are the same as used in the first exemplary embodiment according to FIGS. 1 to 6. Likewise, the monomer liquid 3 is contained in an identical ampoule 5 that can be fractured and is made of glass or a plastic material as the monomer liquid container for the monomer liquid 3, whereby the ampoule 5 is plugged into the receptacle 52. The cartridge 51 forms a cylindrical internal space 61 on its inside that contains the bone cement powder 4. Accordingly, the bone cement applicator is also well-suited for storage of the monomer liquid 3 and bone cement powder 4.

The cartridge 51 comprises a cartridge lid 56 as a cartridge head on its front side (on the bottom in the figures). A dispensing opening is provided in the cartridge lid 56. A mixing rod 57 is fastened to the front side of the receptacle 52 and extends from the front side of the receptacle 52 up into the front part of the cartridge 51, in which the bone cement powder 4 is situated.

The receptacle 52 comprises an external thread 59 on its outside. The receptacle 52 is shaped, in a rear region, in the way of a threaded tube and comprises, on its inside, a cylindrical chamber into which the ampoule 5 is plugged. In a front area, the receptacle 52 is cylinder-shaped on its outside, whereby four projecting strips 97 are provided on the external surface of the receptacle 52 parallel to the cylinder axis of the receptacle 52. The ampoule 5 has a cylindrical ampoule body with a diameter that matches the inside of the receptacle 52. On the inside of the cartridge 51, the cartridge 51 forms the cylindrical internal space 61. The cylinder geometry of the internal space 61 and of the chamber of the receptacle 52 corresponds to cylinders with a circular footprint.

A mixer 60 is fastened to the front side of the mixing rod 57 in the form of mixing vanes with a surrounding scraping ring. The presence of a scraping ring allows the areas right at the internal wall of the internal space 61 to be reached.

The receptacle 52 is bordered on its front side by a wall with multiple passages 86 as a closure of the front side, whereby the wall on the front side of the receptacle 52 closes the chamber toward the front at its circular base surface. A dispensing plunger 62 is arranged in the internal space 61 of the cartridge 51 so as to be mobile in the axial direction of the cylindrical internal space 61, and is arranged in the internal space 61 in a press-fit. The mixing rod 57 is guided through a central passage in the dispensing plunger 62 such that the mixing rod 57 can be moved against the dispensing plunger 62 without the dispensing plunger 62 moving in the internal space 61 of the cartridge 51 in this context. With the receptacle 52 retracted, the mixer 60 touches against the front side of the dispensing plunger 62. As a result, the mixer 60 can reach the entire front part of the internal space 61 that is bordered on the side by the cartridge 51, on the front by the cartridge lid 56, and in the rear by the dispensing plunger 62. As a result, complete mixing of the bone cement powder 4 with the monomer liquid 3 in this area is ensured.

The dispensing plunger 62 comprises multiple channels 64 passing through the dispensing plunger 62, which are arranged in a ring-shape about the central passage for the mixing rod 57 in the dispensing plunger 62 and connect the front side of the dispensing plunger 62 to the rear side of the dispensing plunger 62 and thereby connect the two sides of the internal space 61 of the cartridge 51 to each other. The channels 64 are covered by a ring-shaped pore filter 66. The pore filter 66 is impermeable to the bone cement powder 4 from the internal space 61 of the cartridge 51, and is permeable to the monomer liquid 3 and gases. As a result, the bone cement powder 4 is prevented from ingress into the inside of the receptacle 52.

The dispensing plunger 62 comprises a larger external diameter than the external thread 59 of the receptacle 52. The external diameter of the cylindrical dispensing plunger 62 fits the internal diameter of the internal space 61 of the cartridge 51. The dispensing plunger 62 seals the internal space 61 of the cartridge 51.

An opening facility 68 is provided on the rear side of the receptacle 52 and can be used to push the ampoule 5 in the direction of the dispensing plunger 62 in order to open the ampoule 5 on the inside of the receptacle 52 such that the monomer liquid 3 in the receptacle 52 flows out. For this purpose, the opening facility 68 comprises a two-step sleeve 70, whereby the front side of the sleeve 70 forms a hollow cylinder in which an ampoule head of the ampoule 5 is arranged. The sleeve 70 of the opening facility 68 can thus push onto the shoulders 21 of the ampoule 5 in order to push the ampoule 5 to the front in the direction of the dispensing plunger 62 and to thus open it. Because the sleeve 70 presses onto the shoulders 21, the force is guided through the ampoule body to an ampoule base 27 of the ampoule 5. The walls of the ampoule body are very stable such that the ampoule 5 will not fracture in this area. The ampoule 5 can thus be fractured at the ampoule base 27.

In this context, the sleeve 70 touches against the internal wall of the receptacle 52 and covers it in the area of the rear side of the inside of the receptacle 52. The rear-side end of the receptacle 52 is covered by a closure cap 72 of the opening facility 68. A wall perpendicular to the axis of the cylinder geometry of the sleeve 70 is provided in the sleeve 70, whereby an opening 73 is provided in the wall. The opening 73 prevents a gas spring from being formed during the insertion of the receptacle 52 into the cartridge 51. Moreover, the monomer liquid 3 can flow more easily out of the receptacle 52 if air can flow through the opening 73. For application, the bone cement applicator needs to be held or set up with the cartridge lid 56 facing downwards, as is shown in FIGS. 7 to 12. The sleeve 70 is fastened to the screw-type closure cap 72. The closure cap 72 comprises an internal thread 74 that fits the external thread 59 of the receptacle 52.

The closure cap 72, or the opening facility 68 as it may be, is screwed a way, but not all the way to a limit stop, onto the rear side of the receptacle 52 and is thus fastened to the receptacle 52. It is important that the closure cap 72 can be screwed further onto the receptacle 52 and that the sleeve 70 can be inserted more deeply into the receptacle 52 by this configuration to allow the ampoule 5 to be opened in the receptacle 52.

On the rear side of the receptacle 52, a circumferential groove is provided in the external thread 59, into which a securing element 76 in the form of a brace is plugged. The securing element 76 prevents the closure cap 72 from being screwed onto the receptacle 52 inadvertently and thus prevents the opening facility 68 from being operated inadvertently. The securing element 76 can be detached right before a use of the bone cement applicator by pulling off the securing element 76. The opening facility 68 can then be screwed into the receptacle 52.

In order to prevent the closure cap 72 from rotating in the wrong direction and thus to prevent the receptacle 52 from being opened on its rear side, a reverse motion lock is provided (not shown in FIGS. 7 to 12). The reverse motion lock prevents the closure cap 72 from detaching and/or the opening facility 68 from detaching from the receptacle 52. The reverse motion lock can be implemented, for example, as a screw lock in the form of a locking disk or by a pair of wedge lock disks or similar measures.

In order to be able to conveniently rotate the opening facility 68 and the receptacle 52 by hand and in order to be able to conveniently insert and pull out the receptacle 52 into and out of the cartridge 51, the rear-side end thereof is fitted with a handle 78. For sealing the sleeve 70 with respect to the internal wall of the receptacle 52, two circumferential seals 80 made of rubber are arranged in circumferential grooves on the front-most external circumference of the sleeve 70. The sleeve 70 is graduated on the outside and thus forms a limit stop in addition to the limit stop formed by the closure cap 72, whereby the limit stops prevent the opening facility 68 from being screwed further onto and/or into the receptacle 52.

Likewise, the external circumference of the dispensing plunger 62 has two grooves arranged on it, in which two circumferential seals 82 made of rubber are situated and which are situated at a distance from each other in the longitudinal direction. The seals 82 seal the dispensing plunger 62 with respect to the internal space 61 of the cartridge 51 and separate the internal space 61 of the cartridge 51 into a front part, in which the bone cement powder 4 is arranged, and a rear part.

A mandrel 84 for fracturing the ampoule 5 is arranged on the front wall of the receptacle 52 that points to the cartridge lid 56. For this purpose, the mandrel 84 points into the inside of the receptacle 2. In order to open the ampoule 5, the ampoule 5 can be pushed, by the sleeve 70, onto the mandrel 84 until the ampoule base 27 of the ampoule 5 is pushed into the ampoule body. The mandrel 84 has a blunt tip whose purpose is to have the force act on the ampoule 5 on a middle area of the ampoule base 27 such that a predetermined breakage site in the connection between the ampoule base 27 and the side walls of the ampoule body is used. The force for this purpose is exerted via the sleeve 70. The sleeve 70 has approximately the same diameter as the ampoule body of the ampoule 5. The ampoule head of the ampoule 5 is arranged on the inside of the sleeve 70 in this context. What this attains is that the ampoule 5 is not fractured in the area of the sleeve 70, because the cylindrical ampoule body is very stable, whereas the mandrel 84 can be pushed relatively easily from the front into the ampoule 5.

The mixing rod 57 is fastened to the receptacle 52 inside the mandrel 84. The mandrel 84 is connected to the receptacle 52 by a predetermined breakage site such that a pressure exerted on the mixing rod 57 causes the mixing rod 57 to sever the mandrel 84 from the receptacle 52 such that the mixing rod 57 with the mandrel 84 at the tip can be moved through the front base surface of the receptacle 52. Alternatively, an internal circular disk (not shown) of the front side of the receptacle 52 can be connected to the receptacle 52 by a thread such that the mandrel 84 can be separated, by the circular disk, from the remaining receptacle 52 by a rotation of the receptacle 52 against the mixing rod 57, which is affixed to the cartridge lid 56 for this purpose, such that the mixing rod 57 again can be moved with respect to the remaining receptacle 52.

Figure 10:
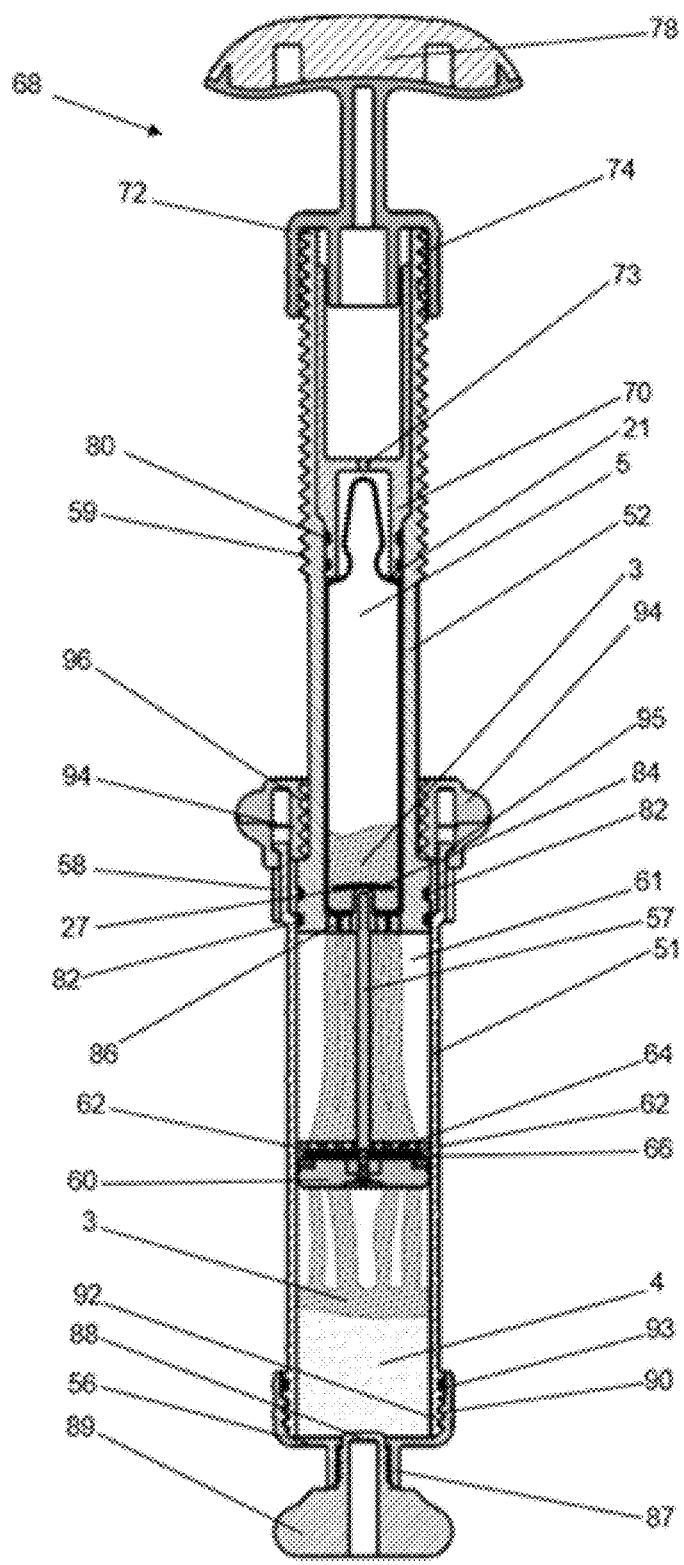
FIG. 10 is a schematic cross-sectional view of the second bone cement applicator according to the invention as shown in FIG. 9 with an opened monomer liquid container.

Multiple passages 86 are arranged about the mandrel 84 and connect the inside of the receptacle 51 to the internal space 61 of the cartridge 51. The monomer liquid 3 can flow through the passages 86 into the internal space 61 of the cartridge 51, as is shown in FIG. 10.

The front side of the cartridge 51 is closed by the cartridge lid 56. A socket 87 bordering the dispensing opening in the cartridge lid 56 is formed in the middle of the cartridge lid 56. A closure 88 for closing the dispensing opening is screwed into the socket 87 and is thus fastened in a detachable manner. The closure 88 can be operated via wings 89 in the way of a wing screw. The cartridge lid 56 is screwed onto an external thread 92 on the front side of the cartridge 51 by an internal thread 90. The cartridge lid 56 is additionally sealed with respect to the cartridge 51 by a circumferential seal 93.

The front part of the internal space 61 of the cartridge 51 has the mixer 60 arranged in it, by which the content of the front part of the internal space 61 can be mixed through a manual motion of the mixer 60. The manual motion of the mixer 60 takes place by inserting and pulling out the receptacle 52 into and from the cartridge 51. Namely, this action also causes the mixing rod 57, which is fastened to the front side of the receptacle 52, to be moved back and forth in a linear manner. In this context, the mixing rod 57 moves through the feedthrough in the dispensing plunger 62, and the mixer 60 fastened to the mixing rod 57 moves in the front part of the internal space 61 of the cartridge 51.

A two-part sliding ring 94 is fastened to the rear side of the cartridge 51. A limit stop 95 on the rear side of the cartridge 51 prevents the sliding ring 94 from being separated from the cartridge 51. The two parts of the sliding ring 94 are connected firmly to each other in order to be able to assemble the sliding ring 94 onto the limit stop 95. The external wall of the cartridge 51 has grooves 58, which engage the projections of the sliding ring 94, provided in the area of the sliding ring 94, such that the sliding ring 94 is linearly mobile only along the grooves 58. The sliding ring 94 has an internal thread 96 on its inside that matches the external thread 59 of the receptacle 52. Accordingly, the receptacle 52 can be screwed into the internal thread 96 of the sliding ring 94 (see FIG. 12).

In addition, the internal thread 96 of the sliding ring 94 serves as a limit stop for the insertion of the receptacle 52 into the cartridge 51. Namely, when the receptacle 52 is inserted into the cartridge 51 up to the limit stop, the external thread 59 of the receptacle 52 meets the internal thread 96 of the sliding ring 94, which is pushed fully in the direction of the cartridge lid 56. Concurrently, the length of the mixing rod 57 is selected appropriately such that the mixer 60 touches against the cartridge lid 56 at the front side of the internal space 61. By this configuration, the bone cement 48 at the front side of the internal space 61 can also be reached and mixed by the mixer 60.

The closure 88 projects a little ways into the internal space 61 of the cartridge 51. A recess accommodating the part of the closure 88 that projects into the internal space 61 is provided on the front side of the mixer 60 that faces the cartridge lid 56. By this configuration, the bone cement 48 touching against the closure 88 and against the cartridge lid 56 can also be mixed, and having this recess also provides a free cross-section of flow to the bone cement 48, when the closure 88 is removed and the mixer 60 touches against the cartridge lid 56 during the dispensation of the bone cement 48 (see FIG. 12).

The work-flow of a method according to the invention is described in the following based on FIGS. 7 to 12. Initially, the bone cement applicator is in the starting state (see FIGS. 7 and 8). In this state, the bone cement applicator has been packaged and sterilized with ethylene oxide. The ethylene oxide can enter into the inside of the receptacle 52 through gaps in the opening facility 68 and through the opening 73 and can enter into the internal space 61 of the cartridge 51 through the passages 86, the pore filter 66, and the channels 64. The gas exchange takes place in a vacuum chamber or negative pressure chamber in this context. In this state (see FIGS. 7 and 8), the bone cement applicator is unpacked.

Figure 9:
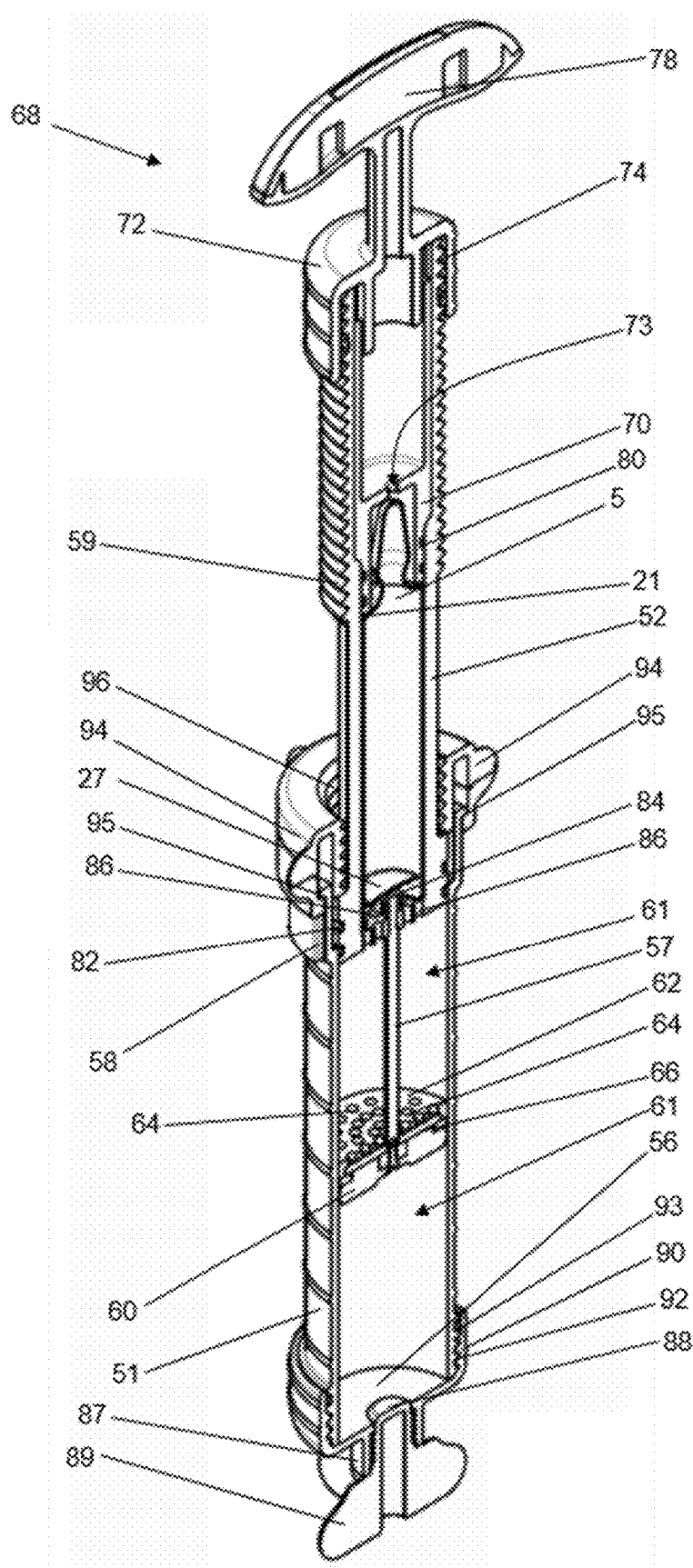
FIG. 9 is a schematic prospective cross-sectional view of the second bone cement applicator according to the invention as shown in FIGS. 7 and 8 without the starting components, having an opened monomer liquid container for illustration of the work-flow of a method according to the invention.

The securing element 76 is pulled off first. The bone cement applicator is held with the cartridge lid 56 downwards. Subsequently, the opening facility 68 is screwed into the receptacle 52. As before, the bone cement applicator is held with the cartridge lid 56 downwards. In this context, the sleeve 70 pushes the shoulders 21 of the ampoule 5 in a downward direction. Subsequently, the ampoule 5 is pushed onto the mandrel 84 by its ampoule base 27, and the ampoule 5 fractures at its ampoule base 27. This scenario is shown in FIGS. 9 and 10.

The monomer liquid 3 exits from the opened ampoule 5 in the area of the passages 86. Because the bone cement applicator is held with the cartridge lid 56 downwards, the monomer liquid 3 driven by gravity immediately flows downwards through the passages 86, the pore filter 66, and the channels 64 into the internal space 61 of the cartridge 51 and distributes in the bone cement powder 4 (see FIG. 10). In order to accelerate the monomer transfer, the receptacle 52 can be pushed into and pulled out of the cartridge 51.

The mixing of the bone cement 48 and/or of the starting components 3, 4 of the bone cement 48 takes place by inserting and pulling out the receptacle 52 into and out of the cartridge 51, while the mixer 60 moves simultaneously in the internal space 61 of the cartridge 51. In this context, the mixer 60 reaches all spaces in the internal space 61 between the dispensing plunger 62 and the cartridge lid 56. To guide this motion, the strips 97 touching against the internal thread 96 of the sliding ring 94 are arranged on the outside of the receptacle 52 in the front area with no external thread 59. The strips 97 prevent the receptacle 52 from wobbling during the mixing process. The gaps allow air to escape that would otherwise be enclosed between the sliding ring 94, the external wall of the receptacle 52, the internal wall of the cartridge 51, and the seal 82. This prevents having to work against the force of a gas spring in this area while the bone cement 48 and/or the starting components 3, 4 are being mixed.

Figure 11:
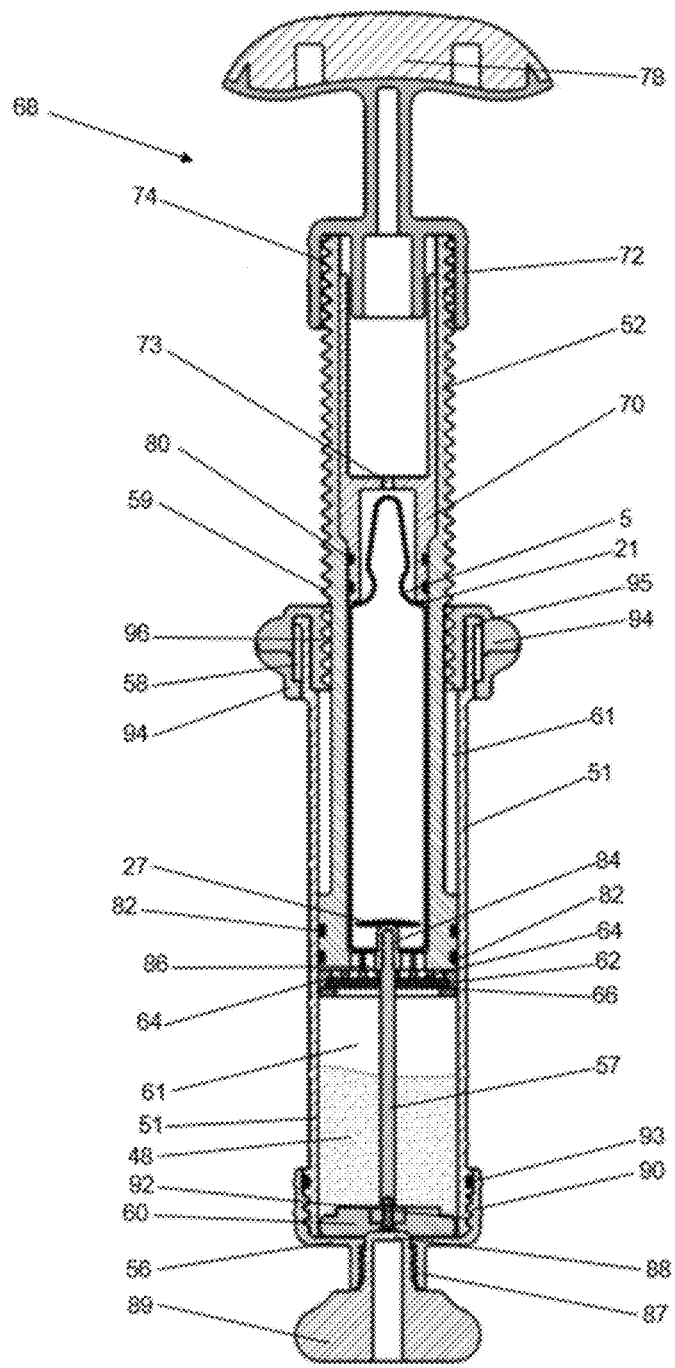
FIG. 11 is a schematic cross-sectional view of the second bone cement applicator according to the invention as shown in FIGS. 7 to 11 having the receptacle inserted into the cartridge for illustration of the work-flow of a method according to the invention.
Figure 12:
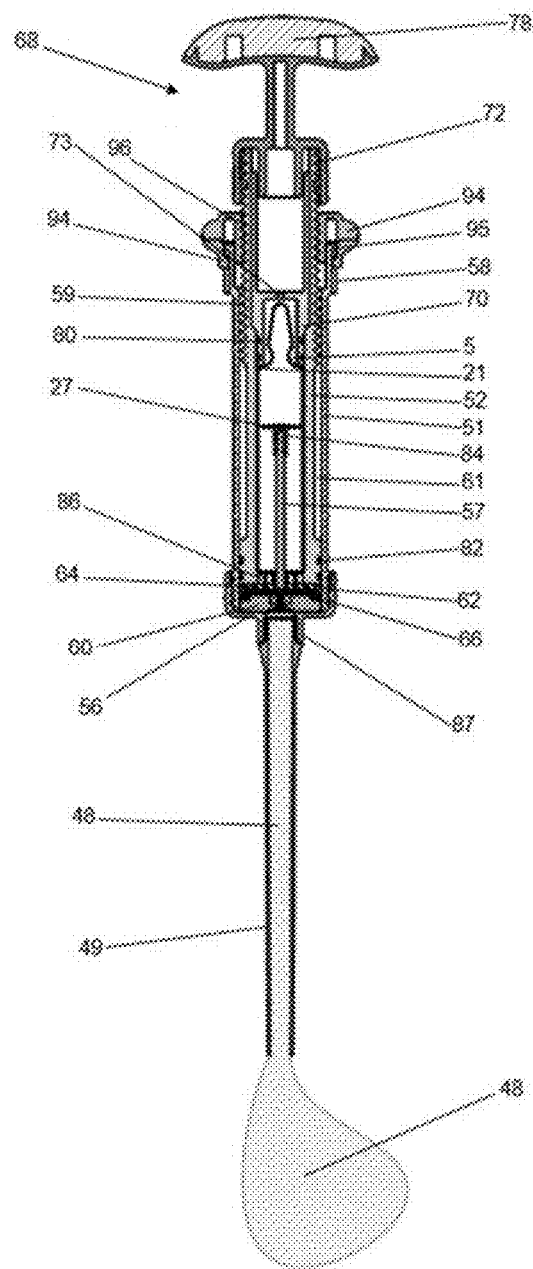
FIG. 12 is a schematic cross-sectional view of the second bone cement applicator according to the invention as shown in FIGS. 7 to 11 having the receptacle screwed into the cartridge after dispensation of the bone cement for illustration of the work-flow of a method according to the invention.

Finally, the bone cement 48 is successfully mixed and the receptacle 52 is inserted fully into the cartridge 51 so that the mixer 60 touches against the cartridge lid 56. This scenario is shown in FIG. 11.

In order to be able to screw the receptacle 52 into the internal thread 96 of the sliding ring 94, the sliding ring 94 is pulled out of the cartridge 1 up to the limit stop 95 after the bone cement 48 has been mixed. As a result, the internal thread 96 of the sliding ring 94 can engage the external thread 59 of the receptacle 52. The sliding ring 94 cannot be detached completely from the cartridge 51 because of the limit stop 95. By this configuration, the receptacle 52 can be screwed into the sliding ring 94 and thus into the cartridge 51. As a result, the receptacle 52 can be pushed forcefully into the cartridge 51. The front of the mixer 60 touches against the cartridge lid 56 such that the mixing rod 57 cannot get out of the way. The pressure transmitted by the mixing rod 57 detaches the mandrel 84 from the front wall of the receptacle 52 or the mixing rod 57 punctures the mandrel 84. Concurrently, the dispensing plunger 62, which is supported in a press fit, is detached from the receptacle 52 and driven in the direction of the cartridge lid 56.

When the receptacle 52 is screwed further into the cartridge 51, the bone cement 48 is expelled out of the internal space 61 of the cartridge 51 through the opened dispensing opening. For this purpose, the closure 88 is first unscrewed from the dispensing opening and the dispensing tube 49 is screwed into the internal thread of the socket 87. For this purpose, the dispensing tube 49 has an external thread that matches the internal thread of the socket 87. The bone cement 48 is pressed between the mixer 60 and the cartridge 56, through the dispensing opening and the socket 87 into the dispensing tube 49. Subsequently, the bone cement 48 flows out of the dispensing tube 49 and is ready for application (see FIG. 12).

During the extrusion of the bone cement 48, gas inclusions in the bone cement 48 are pushed upwards into the receptacle 52 through the pore filter 66 such that a gas-depleted bone cement 48 is produced.

As an alternative to the dispensing tube 49, a hose with a trocar (not shown) can be fastened to the socket 87 through which the bone cement 48 can be applied under X-ray control in places that are difficult to access.

The features of the invention disclosed in the preceding description and in the claims, figures, and exemplary embodiments, can be essential for the implementation of the various embodiments of the invention both alone and in any combination.

Although illustrated and described above with reference to certain specific embodiments and examples, the present disclosure is nevertheless not intended to be limited to the details shown. Rather, various modifications may be made in the details within the scope and range of equivalents of the claims and without departing from the spirit of the disclosure. It is expressly intended, for example, that the steps of the methods of using the various devices disclosed above are not restricted to any particular order unless otherwise noted.

What is claimed:

1. A bone cement applicator for storage and mixing of a bone cement powder and a monomer liquid as well as for applying a pasty bone cement mixed together from the bone cement powder and the monomer liquid, the bone cement applicator comprising:
    a cartridge defining a cylindrical internal space with a cylinder axis in which the bone cement is mixed, the cartridge having a front side, a cartridge head located on the front side with a dispensing opening for expulsion of the bone cement from the internal space, and a rear side situated opposite from the front side;
    a dispensing plunger for expelling the mixed bone cement from the internal space through the dispensing opening, the dispensing plunger arranged in the internal space of the cartridge so as to be mobile along the cylinder axis of the internal space in the direction of the cartridge head, whereby the bone cement powder is contained between the dispensing plunger and the cartridge head in the internal space of the cartridge;
    a receptacle defining an inside, having a front side that faces the cartridge head, and being both plugged into the cartridge on the rear side of the cartridge and mobile in the cartridge;
    a monomer liquid container arranged on the inside of the receptacle and configured to be opened on the inside of the receptacle, the monomer liquid container containing the monomer liquid; and
    a mixing rod detachably connected to the receptacle, having a first side that faces the cartridge head and to which a mixer is fastened and a second side opposite from the first side and to which the front side of the receptacle is connected, and being arranged in the internal space of the cartridge, such that the mixing rod and the mixer can be moved in the internal space of the cartridge for mixing the bone cement powder with the monomer liquid through a motion of the receptacle against the cartridge, wherein, when the mixing rod is detached from the receptacle and the receptacle is propelled in the direction of the cartridge head the mixing rod can be pushed into the receptacle,
    wherein the front side of the receptacle forms the dispensing plunger and the dispensing plunger is cylindrical.

2. The bone cement applicator according to claim 1, wherein the mixing rod is detached from the receptacle by pressing onto the mixer touching against the cartridge head and/or by rotating or screwing the receptacle against the mixer, which is secured against rotation in the internal space.

3. The bone cement applicator according to claim 1, wherein:
    the dispensing plunger has a feedthrough and is configured to be pushed in the direction of the cartridge head by the receptacle;
    the cartridge head and the dispensing plunger form a border defining a front part of the internal space of the cartridge, in which the mixer and the bone cement powder are arranged, and the dispensing plunger and the receptacle form a border defining a rear part of the internal space of the cartridge separated from the front part; and
    the mixing rod is configured to be guided through the feedthrough of the dispensing plunger and to be axially mobile in the feedthrough.

4. The bone cement applicator according to claim 1, wherein the dispensing plunger has at least one channel that is impermeable to the bone cement powder and is permeable to the monomer liquid and gases.

5. The bone cement applicator according to claim 1, further comprising a second limit stop and a ring having an internal thread and being located on the rear side of the cartridge, wherein the receptacle has an external thread forming a first limit stop, the cartridge has an internal thread on the rear side of the cartridge, the receptacle is configured to be inserted into the internal space up to the first limit stop and to be screwed up to the second limit stop by the external thread into the internal thread of the cartridge or into the internal thread of the ring, the mixing rod cannot be detached from the receptacle during motion of the receptacle up to the first limit stop, and the mixing rod can be detached from the receptacle by screwing the receptacle into the cartridge.

6. The bone cement applicator according to claim 1, further comprising an opening facility arranged on the receptacle, adapted to be operated from outside the bone cement applicator, and configured to open the monomer liquid container on the inside of the receptacle.

7. The bone cement applicator according to claim 1, wherein the inside of the receptacle is connected in a liquid-permeable manner to the internal space of the cartridge, the front side of the receptacle has at least one liquid-permeable passage, and the dispensing plunger has at least one liquid-permeable channel.

8. The bone cement applicator according to claim 1, wherein the cartridge head is a cartridge lid having a socket and the cartridge lid is configured to be screwed onto the cartridge, the cartridge lid seals the internal space of the cartridge at the front side of the cartridge in a gas-tight and liquid-tight manner, and the dispensing opening is arranged in the socket of the cartridge lid.

9. The bone cement applicator according to claim 1, wherein the cartridge has, on its rear side, an internal thread or a ring with an internal thread and the receptacle has an external thread matching the internal thread of the cartridge or the internal thread of the ring and enabling the receptacle to be screwed into engagement with the cartridge.

10. The bone cement applicator according to claim 1, further comprising a mandrel for opening the monomer liquid container, the mandrel arranged on a side of the receptacle that points into the inside of the receptacle.

11. The bone cement applicator according to claim 1, wherein the mixing rod has a circular disk with an external thread and the front side of the receptacle has an internal thread that matches the external thread on the circular disk, whereby the external thread of the circular disk engages the matching internal thread of the front side of the receptacle to connect the mixing rod to the receptacle.

12. The bone cement applicator according to claim 11, wherein the external thread of the circular disk and the internal thread of the front side of the receptacle are left-hand threads.

13. The bone cement applicator according to claim 1, wherein the receptacle has a rear side opposite from the cartridge head with a diameter larger than the internal space of the cartridge.

14. The bone cement applicator according to claim 1, further comprising a ring having an internal thread and being connected to the rear side of the cartridge so as to be mobile by shifting or screwing the ring against the cartridge in the axial direction with respect to the cylinder axis of the cylindrical internal space of the cartridge.

15. The bone cement applicator according to claim 14, wherein the receptacle has an external thread that matches the internal thread of the ring.

16. A bone cement applicator for storage and mixing of a bone cement powder and a monomer liquid as well as for applying a pasty bone cement mixed together from the bone cement powder and the monomer liquid, the bone cement applicator comprising:
    a cartridge defining a cylindrical internal space with a cylinder axis in which the bone cement is mixed, the cartridge having a front side, a cartridge head located on the front side with a dispensing opening for expulsion of the bone cement from the internal space, and a rear side situated opposite from the front side;
    a dispensing plunger for expelling the mixed bone cement from the internal space through the dispensing opening, the dispensing plunger arranged in the internal space of the cartridge so as to be mobile along the cylinder axis of the internal space in the direction of the cartridge head, whereby the bone cement powder is contained between the dispensing plunger and the cartridge head in the internal space of the cartridge;
    a receptacle defining an inside, having a front side that faces the cartridge head, and being both plugged into the cartridge on the rear side of the cartridge and mobile in the cartridge;
    a monomer liquid container arranged on the inside of the receptacle and configured to be opened on the inside of the receptacle, the monomer liquid container containing the monomer liquid; and
    a mixing rod detachably connected to the receptacle, having a first side that faces the cartridge head and to which a mixer is fastened and a second side opposite from the first side and to which the front side of the receptacle is connected, and being arranged in the internal space of the cartridge, such that the mixing rod and the mixer can be moved in the internal space of the cartridge for mixing the bone cement powder with the monomer liquid through a motion of the receptacle against the cartridge, wherein, when the mixing rod is detached from the receptacle and the receptacle is propelled in the direction of the cartridge head the mixing rod can be pushed into the receptacle,
wherein the dispensing plunger has at least one channel that is impermeable to the bone cement powder and is permeable to the monomer liquid and gases.

17. A bone cement applicator for storage and mixing of a bone cement powder and a monomer liquid as well as for applying a pasty bone cement mixed together from the bone cement powder and the monomer liquid, the bone cement applicator comprising:
    a cartridge defining a cylindrical internal space with a cylinder axis in which the bone cement is mixed, the cartridge having a front side, a cartridge head located on the front side with a dispensing opening for expulsion of the bone cement from the internal space, and a rear side situated opposite from the front side;
    a dispensing plunger for expelling the mixed bone cement from the internal space through the dispensing opening, the dispensing plunger arranged in the internal space of the cartridge so as to be mobile along the cylinder axis of the internal space in the direction of the cartridge head, whereby the bone cement powder is contained between the dispensing plunger and the cartridge head in the internal space of the cartridge;
    a receptacle defining an inside, having a front side that faces the cartridge head, and being both plugged into the cartridge on the rear side of the cartridge and mobile in the cartridge;
    a monomer liquid container arranged on the inside of the receptacle and configured to be opened on the inside of the receptacle, the monomer liquid container containing the monomer liquid; and
    a mixing rod detachably connected to the receptacle, having a first side that faces the cartridge head and to which a mixer is fastened and a second side opposite from the first side and to which the front side of the receptacle is connected, and being arranged in the internal space of the cartridge, such that the mixing rod and the mixer can be moved in the internal space of the cartridge for mixing the bone cement powder with the monomer liquid through a motion of the receptacle against the cartridge, wherein, when the mixing rod is detached from the receptacle and the receptacle is propelled in the direction of the cartridge head the mixing rod can be pushed into the receptacle, wherein the inside of the receptacle is connected in a liquid-permeable manner to the internal space of the cartridge, the front side of the receptacle has at least one liquid-permeable passage, and the dispensing plunger has at least one liquid-permeable channel.

18. The bone cement applicator according to claim 17, wherein the dispensing plunger has at least one channel that is impermeable to the bone cement powder and is permeable to the monomer liquid and gases.

19. The bone cement applicator according to claim 17, further comprising an opening facility arranged on the receptacle, adapted to be operated from outside the bone cement applicator, and configured to open the monomer liquid container on the inside of the receptacle.

20. The bone cement applicator according to claim 17, further comprising a mandrel for opening the monomer liquid container, the mandrel arranged on a side of the receptacle that points into the inside of the receptacle.

* * * * *